US008227581B2

(12) United States Patent
Savage et al.

(10) Patent No.: US 8,227,581 B2
(45) Date of Patent: Jul. 24, 2012

(54) MODIFIED α-GALACTOSYL CERAMIDES FOR STAINING AND STIMULATING NATURAL KILLER T CELLS

(75) Inventors: Paul B. Savage, Mapleton, UT (US); Luc Teyton, Del Mar, CA (US); Albert Bendelac, Chicago, IL (US)

(73) Assignees: The Scripps Research Institute, La Jolla, CA (US); The University of Chicago, Chicago, IL (US); Brigham Young University, Provo, UT (US)

( * ) Notice: Subject to any disclaimer, the term of this patent is extended or adjusted under 35 U.S.C. 154(b) by 576 days.

(21) Appl. No.: 12/296,169

(22) PCT Filed: Apr. 9, 2007

(86) PCT No.: PCT/US2007/066250
§ 371 (c)(1),
(2), (4) Date: Nov. 5, 2008

(87) PCT Pub. No.: WO2007/118234
PCT Pub. Date: Oct. 18, 2007

(65) Prior Publication Data
US 2009/0047299 A1 Feb. 19, 2009

Related U.S. Application Data

(60) Provisional application No. 60/790,096, filed on Apr. 7, 2006.

(51) Int. Cl.
*A61K 39/00* (2006.01)
*A61K 39/7028* (2006.01)
*A61K 38/17* (2006.01)
*C07H 15/04* (2006.01)

(52) U.S. Cl. ........ 536/1.11; 536/17.9; 514/1.1; 514/2.4; 514/25; 424/184.1

(58) Field of Classification Search .................. 514/1.1, 514/2.4, 25; 536/17.9; 424/184.1
See application file for complete search history.

(56) References Cited

U.S. PATENT DOCUMENTS

| | | | |
|---|---|---|---|
| 5,242,800 A | 9/1993 | Jimenez et al. | |
| 5,604,207 A | 2/1997 | DeFrees et al. | |
| 5,767,092 A | 6/1998 | Koezuka et al. | |
| 5,780,441 A | 7/1998 | Higa et al. | |
| 5,785,975 A | 7/1998 | Parikh | |
| 5,849,716 A | 12/1998 | Akimoto et al. | |
| 5,936,076 A | 8/1999 | Higa et al. | |
| 5,958,426 A | 9/1999 | Moreau et al. | |
| 6,054,433 A | 4/2000 | Elias et al. | |
| 6,071,884 A | 6/2000 | Koezuka et al. | |
| 6,417,167 B1 | 7/2002 | Maruyama et al. | |
| 6,531,453 B1 | 3/2003 | Taniguchi et al. | |
| 6,610,835 B1 | 8/2003 | Liotta et al. | |
| 6,635,622 B2 | 10/2003 | Tomiyama et al. | |
| 6,747,010 B2 | 6/2004 | Taniguchi et al. | |
| 7,273,852 B2 | 9/2007 | Tsuji et al. | |
| 7,273,853 B2 | 9/2007 | Or et al. | |
| 7,645,873 B2 * | 1/2010 | Savage et al. | 536/53 |
| 7,989,423 B2 * | 8/2011 | Savage et al. | 514/25 |
| 2002/0115624 A1 | 8/2002 | Behar et al. | |
| 2003/0139351 A1 | 7/2003 | Taniguchi et al. | |
| 2003/0153514 A1 | 8/2003 | Yagita | |
| 2003/0157135 A1 | 8/2003 | Tsuji et al. | |
| 2004/0127429 A1 | 7/2004 | Tsuji | |
| 2004/0166554 A1 | 8/2004 | Chamoles | |
| 2004/0266726 A1 | 12/2004 | Yagita | |
| 2005/0192248 A1 | 9/2005 | Tsuji et al. | |
| 2005/0222048 A1 | 10/2005 | Tsuji et al. | |
| 2006/0019246 A1 | 1/2006 | Tsuji et al. | |
| 2006/0073118 A1 | 4/2006 | Bendelac et al. | |
| 2006/0211856 A1 | 9/2006 | Tsuji et al. | |
| 2008/0095787 A1 | 4/2008 | Teyton | |
| 2008/0279894 A1 | 11/2008 | Teyton et al. | |

FOREIGN PATENT DOCUMENTS

| | | |
|---|---|---|
| EP | 0988860 | 3/2000 |
| EP | 1016409 | 7/2000 |
| WO | WO 99/33475 | 7/1999 |
| WO | WO 03/009812 | 2/2003 |
| WO | WO 03/018039 | 3/2003 |
| WO | WO 03/105769 | 12/2003 |
| WO | WO 2004/094444 | 11/2004 |
| WO | WO 2005/000348 | 1/2005 |
| WO | WO 2005/102049 | 11/2005 |
| WO | WO 2006/026389 | 3/2006 |
| WO | WO 2006/029010 | 3/2006 |
| WO | WO 2006/083671 | 8/2006 |
| WO | WO 2007/007946 | 1/2007 |
| WO | WO 2007/050668 | 5/2007 |
| WO | WO 2008/005824 | 1/2008 |
| WO | WO 2008/080926 | 7/2008 |

OTHER PUBLICATIONS

Liu et al, Journal of Immunological Methods, 2006, 312, 34-39; available online Mar. 6, 2006.*
Supplemental European Search Report mailed Sep. 3, 2010.
Liu et al., *Journal of Immunological Methods*, "A modified alpha-galactosyl ceramide for staining and stimulating natural killer T cells." Mar. 2006, pp. 34-39.
Fuji et al., *Clinical Cancer Research*, vol. 6, No. 8, 2000, pp. 3380-3387.
Yamaguchi et al., *Oncology Research, Pergamon Press*, "Enhancing Effects of (2S, 3S, 4R)-1-0-0 Alpha-D-Galactopyranosyl)-2-(N-Hexacosanoylamino)-1,3,4-Octadecanetriol (KRN7000) On Antigen-Presenting Function of Antigen-Presenting Cells and Antimetastatic Activity of KRN7000-Pretreated Antigen-Presenting Cells.", Jan. 1996, vol. 8, No. 10-11, pp. 399-407.
Ando et al., "Solid-phase capture-release strategy applied to oligosaccharide synthesis on a soluble polymer support," *Agnew. Chem.Int.Ed.* (2001) 40:4725-4728.

(Continued)

*Primary Examiner* — Shaojia Anna Jiang
*Assistant Examiner* — Ganapathy Krishnan
(74) *Attorney, Agent, or Firm* — Merchant & Gould P.C.

(57) ABSTRACT

Modified glycolipid compounds are provided. Also disclosed are methods for activating an NKT cell, methods of stimulating an immune response in a subject, and methods suitable for labeling NKT cells.

28 Claims, 10 Drawing Sheets

OTHER PUBLICATIONS

Beaudoin, L. et al., "NKT cells inhibit the onset of diabetes by impairing the development of pathogenic T cells specific for pancreatic beta cells," *Immunity* (2002) 17:725-736.

Bendelac et al., "Increased interleukin 4 and immunoglobulin E production in transgenic mice overexpressing NK1 T cells," *J. Exp. Med.* (1996) 184: 1285-1293.

Bendelac, A. et al., "Autoreactivity by design: innate B and T lymphocytes," 1:177-186. *Natur. Rev. Immunol.* (2001).

Bendelac, A. et al., "The biology of NKT cells," *Ann. Rev. Immunol.* (2007) 25:297-336.

Bendelac, A., "Nondeletional pathways for the development of autoreactive thymocytes," *Nat. Immunol.*(2004) 5:557-558.

Benlagha, K. et al., "In vivo identification of glycolipid antigen-specific T cells using fluorescent CD1d tetramers," *J. Exp. Med.* (2000) 191:1895-1903.

Brigl et al., "Mechanism of CD1d-restricted Immunol. (2003) 4: 1230-1237. natural killer T cell activation during microbial infection," *Nat. Immunol.* (2003) 4: 1230-1237.

Brigl et al., "T cell function and antigen presentation," *Annu. Rev. Immunol.* (2004) 22: 817-890.

Brossay, L. et al., "Cutting edge: structural requirements for galactosylceramide recognition by CD1- restricted NK T cells," *J. Immunol.* (1998) 161(10):5124-5128.

Brutkiewicz et al., "CD1d-mediated antigen presentation to natural killer T (NKT) cells," *Critical Reviews in Immunology* (2003) 23: 403-419.

Brutkiewicz et al., "Natural killer T (NKT) cells and their role in antitumor immunity," *Critical Reviews in Oncology/Hematology* (2002) 41: 287-298.

Cantu et al., "The paradox of immune molecular recognition of alpha-galactosylceramide; low affinity, low specificity for CD1d, high affinity for alpha beta TCRs," *J. Immunol.* (2003) 170: 4673-4682.

Corey et al., "A new method for the synthesis of organic nitro compounds," 106:3682-3683. *J. Am. Chem. Soc.* (1984) 106:3682-3683.

Daoudi, J-M. et al., "New bicyclam-galcer analogue conjugates: synthesis and in vitro anti-HIV activity," *Biorg. Med. Chem. Lett.* (2004) 14:495-498.

Dascher, C.C. et al., "CD1 Antigen Presentation (2003) 10:164-182. and Infectious Disease," *Contributions to Microbiology* (2003) 10:164-182.

Davis, N. J. et al., "Chemical Synthesis of Disaccharides Which are Partial Structures of the Glycosaminoglycan Heparan Sulfate," *J. Chem. Soc.* (1994) 1:359-368.

De Libero, G. et al., "Self glycosphingolipids: new antigens recognized by autoreactive T lymphocytes," *News Physiol. Sci.* (2003) 18:71-76.

European Office Action for Application No. 03816701.1 dated Nov. 29, 2007.

European Office Action for Application No. 05810863.0 dated Apr. 2, 2008 (4 pages).

Fischer, K. et al., "Mycobacterial phosphatidylinositol mannoside is a natural antigen for CD1d-restricted T cells," *Proc. Natl. Acad. Sci. USA* (2004) 101:10685-10690.

Fujii et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.* (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," *J. Clin. Invest.* (2004) 114(10):1379-1388.

Godfrey, D.I. et al., "The elusive NKT cell antigen—is the search over?" *Science* (2004) 306:1687-1688.

Goff, R.D. et al., "Effects of lipid chain lengths in alpha-galactosylceramides on cytokine release by natural killer T cells," *J. Am. Chem. Soc.* (2004) 126:13602-13603.

Goodman & Gilman's the Pharmacological Basis of Therapeutics, Tenth Edition, Hardman and Limbird,.editors, the McGraw-Hill Companies, Inc., New York, (2001) 54-56.

Gui, M. et al., "TCR beta chain influences but does not solely control autoreactivity of V alpha 14J28IT cells," *J.Immunol.* (2001) 167(11):6239-6246.

Gumperz, J.E. et al., "Functional distinct subsets of CD1d-restricted natural killer T cells revealed by CD1d tetramer staining," *J. Exp. Med.* (2002) 195(5):625-636.

Gumperz, J.E. et al., "Murine CD1d-restricted T cell recognition of cellular lipids," *Immunity* (2000) 12:211-221.

Gupta, R.K. et al., "Adjuvants—a balance between toxicity and adjuvanticity," *Vaccine* (1993) 11(3):293-306.

Hashimoto, S. et al., "Glycosylation Using Glucopyranosyl Fluorides and Silicon-Based Catalysts, Solvent Dependency of the Stereoselection," *Tetrahedron Letters* (1984) 25:13:1379-1382.

Hayashi, M. et al., "Simple Synthesis of Glycosyl Fluorides," *Chem. Letters* (1984) 1747-1750.

Hermans, I.F. et al., "Nkt cells enhance CD4+ and CD8+ T cell responses to soluble antigen in vivo through direct interaction with dendritic cells," *J. Immunol.* (2003) 171:5140-5147.

Honey, K. et al., "Thymocyte expression of cathepsin L is essential for NKT cell development," *Nat. Immunol.* (2002) 3:1069-1074.

Iida, N. et al., "A sulfated glucosylceramide from rat kidney," *J. Biol. Chem.* (1989) 264(10):5974-5980.

Islam, I. et al., "Synthesis and antiviral activity of (24(4-(3-((1-methylethyl)amino)-2-pyridy1)-1-piperazinyl)carbony)-1H-indo 1-5-y1) (BHAP) acylspingosine HIV reverse transcriptase inhibitors," *Biorg.Chem.* (1995) 23(4):499-511.

Ismail, N. et al., "Overproduction of TNF-alpha b CD8+ type 1 cells and down-regulation of IFN-γ, production.By CD4+ THL cells contribute to toxic shock-like syndrome in an animal model of fatal monocytotropic.ehrlichiosis," *J. Immunol.* (2004) 172:1786-1800.

Karadimitris, A. et al., "Human CD1d-glycolipid tetramers generated by in vitro oxidative refolding chromatography," *Proc. Natl. Acad. Sci. USA*(2001) 98(6):3294-3298.

Kawano, T. et al., "CD1d-restricted and TCR-mediated activation of Val 4 NKT cells by glycosylceramides," *Science*(1997) 278:1626-1629.

Khan, M. et al., "Syntheses and Antiinflammatory Activity of Some 6-aryl-2,3,4,5-tetrahydro-3-pyridazinones," *Indian J. Chem.*(2000) 39B:614-619.

Kinjo, Y. et al., "Recognition of bacterial glycosphingolipids by natural killer 525. T cells," *Nature*(2005) 434:520-525.

Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," *J. Exp. Med.*(1999) 189:1121-1127.

Ko et al. "a-Galactosylceramide Can Act As a Nasal Vaccine Adjuvant Inducing Protective Immune Responses against Viral Infection and Tumor." *Journal of Immunology*.vol. 175. No. 5. 2005. pp. 3309-3317.

Kronenberg, M., "Toward an understanding of NKT cell biology: progress and paradoxes," *Ann. Rev. Immunol*(2005) 23:877-900.

Lee, P.T. et al., "Testing the NKT cell hypothesis on human IDDM pathogenesis," 110(6):793-800. *J. Clin. Invest.*(2002).

Long et al., "Synthesis and evaluation of stimulatory properties of *Sphingomonadaceae*glycolipids," *Nature Chemical Biology*(2007) 9: 559-564. XP002542183.

Matsuda, J.L. et al., "Tracking the response of natural killer T cells to a glycolipid antigen using CD1d tetramers," *J. Exp. Med.*(2000) 192(5):741-753.

Mattner, J. et al., "Exogenous and endogenous glycolipid antigens activate NKT cells during microbial infections," *Nature*(2005) 434:525-529.

Miyamoto, K. et al., "A Synthetic Glycolipid Prevents Autoimmune Encephalomyelitis by Inducing TH2 Bias of Natural Killer T Cells," *Nature*(2001) 413:531-534.

Morita, M. et al., "Structure-Activity Relationship of α-Galactosylceramides Against B16-Bearing Mice," *J. Med. Chem.* (1995) 38:2176-2187.

Nakagawa, R. et al., "Mechanisms of the Antimetastatic Effect in the Liver and of the Hepatocyte Injury Induced by α-Galactosylceramide in Mice," *J. Immun.*(2001) 166:11:6578-6584.
Pal, E. et al., "Costimulation-Dependent Modulation of Experimental Autoimmune Encephalomyelitis by Ligand Stimulation of Vα14 NK T Cells," *J. Immunol.*(2001) 166:662-668.
Park, S.H. et al., "CD1-restricted T-cell responses and microbial infection," *Nature*(2000) 406:788-792.
Park, S.H. et al., "The Mouse CD1d-restricted Repetoire is Dominated by a Few Autoreactive T cell Receptor Families," *J. Exp. Med.*(2001) 8:893-904.
Park, S.-H. et al., "Tissue-specific recognition of mouse CD1 molecules," *J. Immunol.*(1998) 160:3128-3134.
Petrovsky, N. et al., "Vaccine adjuvants: current state and future trends," *Immunol. Cell Biol.*(2004) 82:488-496.
Prigozy, T.I. et al., "Glycolipid antigen processing for presentation by CD1d 291:664-667. molecules," *Science*(2001).
Rock, K.L. et al., "Natural endogenous adjuvants," *Springer Semin. lmmunopathol.*(2005) 26:231-24.
Sakai, T. et al., "Effects of α, and β-Galactosylated C2-Ceramides on the Immune System," *J. Med. Chem.*(1998) 41:650-652.
Sidobre, S. et al., "CD1d tetramers: a powerful tool for the analysis of glycolipid reactive T cells," *J. Immunol. Methods*(2002) 268:107-121.
Silk et al. "Utilizing the adjuvant properties of Cd1d-dependent NK T cells in T cell-mediated immunotherapy." *Journal of Clinical Investigation.*vol. 114. No. 12. 2004. pp. 1810-1811.
Sinay, P. et al., *Bioorganic and Medicinal Chemistry*(1998) 6: 1337-46.
Singh et al., "The natural killer T Cell ligand Alpha-Galactosylceramide protects mice against EAE by an IL-4-and IL-10- dependent mechanism," *FASEB J., Fed. Of Amer. Soc. For Exp. Bio*(2002) 16: A1043.
Singh, P.P. et al., "The Synthesis of 2,3,4,6,7-Penta-O-Methyl-D-glycero-L-manno-Heptose and 2,4,6,7-TetraO-Methyl-D-glycero-L-manno-Heptose," *Carbohydrate Res.*(1970) 12:261-266.
Smyth, M.J. et al., "NKT cells—conductors of tumor immunity?" *Curr. Opin. Immunol.*(2002) 14(2):165-171.
Smyth, M.J. et al., "NKT cells and tumor immunity—a double-edged sword," 1:459-460. *Nature Immunology*(2001).
Stanic A.K. et al., "Defective presentation of the CD1d1-restricted natural Val4Ja18 NKT lymphocyte antigen caused by Beta-D-glucosylceramide synthase deficiency," *Proc. Natl. Acad. Sci. USA*(2003) 100:1849-1854.
Supplementary Search Report of the European Patent Office for Application No. 03816701.1 dated Sep. 17, 2007.
Takikawa et al., "Diastereoselective Epoxidation of the Double Bond at C-4 of Sphinogosines to Provide Phytosphingosine Relatives such as α-Galactosylceramide KRN7000," *Tetrahedron*(1998) 54:3141-3150.
The Merck Manual, 16$^{th}$ Edition (1999): pp. 339-342 and 1488-1490.
United States Office Action for U.S. Appl. No. 12/624,048 mailed Sep. 29, 2010.
United States Office Action for U.S. Appl. No. 10/550,165 mailed Oct. 27, 2008.
United States Office Action for U.S. Appl. No. 10/550,165 mailed Jan. 9, 2008.
United States Office Action for U.S. Appl. No. 10/550,165 mailed Jul. 20, 2007.
United States Office Action for U.S. Appl. No. 10/550,165 mailed Apr. 12, 2007.
Van Der Vliet, H.J.J. et al., "Effects of a-galactosylceramide (KRN7000), interleukin-12 and interleukin-7 on phenotype and cytokine profile of human Vα24+Vβ11+T cells," *Immunology*(1999) 98:557-563.
Van Kaer, L., "Alpha-galactosylceramide therapy for autoimmune diseases: Rev. Immunol. (2005) 5:31-42. prospects and obstacles," *Nat. Rev. Immunol.*(2005) 5:31-42.
Vandommelen, S.L.H. et al., "Activation of natural killer (NK) T cells during murine cytomegalovirus infection enhances the antiviral response mediated by NK cells," *J. Virology*(2003) 77(3):1877-1884.
Vaultier, M. et al., "Reduction d'azides en amines primaires par une methode generale utilisant la reaction de staudinger," *Tetrahedron Letters*(1983) 24:763 (Not in English).
Wang, B. et al., "CD1-Restricted NK T Cells Protect Nonobese Diabetic Mice from Developing Diabetes," *J.Exp. Med.*(2001) 194:313-319
Wang, F. et al., "Tuning of Binding Selectivity: Metal Control of Organic Guest Binding and Allosteric Perturbation of Fluorescent Metal Sensor," *J. Org. Chem.*(1999) 64:8922-8928.
Weber, G. et al., "Synthesis and Spectral Properties of a Hydrophobic Fluorescent Probe: 6-Propionyl-2- (dimethylamino) naphthalene," *Biochem.*(1979) 18:14:3075-3078.
Winau, F. et al., "Saposin C is required for lipid presentation by human CDIb," 174. *Nat. Immunol.*(2004) 5:169-174.
Wu et al., "Bacterial glycolipids and analogs as antigen for CD1d-restricted NKT 102(5):1351-1356. cells," *PNAS*(2005).
Wu, D.Y. et al., "Cross-presentation of disialoganglioside GD3 to natural killer 198:173-181. T cells," *J. Exp. Med.* (2003).
Xia, C. et al., "Thio-isoglobotrihexosylceramide, an Agonist for activating invariant natural killer T cells," *Org.Lett.* (2006) 8(24):5493-5496
Yu, K.O.A. et al., "Modulation of CD1d-restricted NKT cell responses by using N-acyl variants of alpha-galactosylceramides," *Proc. Natl. Acad. Sci. USA*(2005) 102(9):3383-3388.
Zajonc, D.M. et al., "Structural basis for CD1d presentation of a sulfatide derived from myelin and its implications for autoimmunity," *J. Exp. Med.* (2005) 202(11):1517-1526.
Zajonc, D.M. et al., "Structure and function of a potent agonist for the semi-invariant natural killer T cell receptor," *Nat. Immunol.* (2005) 6:810-818.
Zhou et al., "Synthesis and NKT cell stimulating properties of fluorophore-and biotin-appended 6"-amino-6"deoxy-galactosylceramides," *Org. Lett.* (2002) 4(8):1267-1270. XP003008968.
Zhou, D. et al., "Editing of CD1d-bound lipid antigens by endosomal lipid transfer 303:523-527. proteins," *Science* (2004).
Zhou, D. et al., "Lysosomal glycosphingolipid recognition by NKT cells," *Science*(2004) 306:1786-1789.
Zhou, D., "The immunological function of iGb3," *Curr. Prot. Pept. Sci.* (2006) 7:325-333.
International Search Report for Application No. PCT/US2005/031407.
Written Opinion for Application No. PCT/US2005/031407.
International Search Report for International Application No. PCT/US2007/072451.
Written Opinion for International Application No. PCT/US2007/072451.
International Search Report for International Application No. PCT/US06/002781.
Written Opinion for International Application No. PCT/US06/002781.
International Search Report for International Application No. PCT/US07/66250.
Written Opinion for International Application No. PCT/US07/66250.
International Search Report for International Application No. PCT/US03/08530.
Written Opinion for International Application No. PCT/US03/08530.

* cited by examiner

A)

B)

C)

MODIFIED α-GALACTOSYL CERAMIDES FOR STAINING AND STIMULATING NATURAL KILLER T CELLS

CROSS-REFERENCE TO RELATED APPLICATIONS

This patent application is a national stage filing under 35 U.S.C. 371 of International Application No. PCT/US2007/066250, filed on Apr. 9, 2007, which claims priority benefits to U.S. Provisional Application No. 60/790,096, filed on Apr. 7, 2006, which are incorporated herein by reference in their entireties.

A portion of the work described herein was supported by grant number AI 53725 from the National Institutes of Health. The United States Government has certain rights in the invention.

INTRODUCTION

Natural killer T cells ("NKT cells") are a population of innate-like memory/effector cells that express both natural killer (NK) receptors and a conserved, semi-invariant T cell receptor (TCR), (Vα14-Jα18/Vβ8 in mice and Vα24-Jα18/Vβ11 in humans). NKT cells have been implicated in suppression of autoimmunity and graft rejection, promotion of resistance to pathogens, and promotion of tumor immunity.

NKT cells recognize foreign and self lipid antigens presented by the CD1d member of the family of β2 microglobulin-associated molecules. A variety of lipids with different structures have been shown to bind CD1d molecules in a unique manner that accommodates a fatty acid chain in each of the two hydrophobic binding pockets (A' and F) of the CD1d molecule. Lipid species capable of binding CD1d molecules include mycolic acids, diacylglycerols, sphingolipids, polyisoprenoids, lipopeptides, phosphomycoketides and small hydrophobic compounds. The evolutionary conservation of NKT cells is striking, as mouse NKT cells recognize human CD1d plus glycolipid antigen and vice versa.

NKT cells respond with vigorous cytokine production within hours of TCR activation by releasing $T_{H1}$-type cytokines, including IFN-γ and TNF, as well as $T_{H2}$-type cytokines, including IL-4 and IL-13. Thus, NKT cells exhibit a dual function: they act as immunosuppressive cells via their production of $T_{H2}$-type cytokines; and also act as immune promoters to enhance cell-mediated immunity via the production of $T_{H1}$-type cytokines.

NKT cells have been studied primarily in the context of CD1d presentation of an α-galactosyl ceramide (αGC), termed KRN7000, a glycolipid not considered to be a natural antigen for NKT cells. Isolating and quantifying CD1d responsive NKT cells by flow cytometry has commonly been accomplished using fluorophone-tagged CD1d tetramers loaded with KRN7000. KRN7000 is also used in studies of the influences of NKT cell stimulation on specific disease states. However, supplies of KRN7000, which is derived from a marine sponge, have been limited and this glycolipid has relatively poor solubility in either aqueous or organic solvents.

SUMMARY OF THE INVENTION

Modified α-galactosyl ceramides provided by the invention have been found to stimulate NKT cells more effectively than KRN7000, both in vitro and in vivo. In addition, these molecules may display increased solubility and enhanced loading into CD1d tetramers.

In one aspect, the invention provides a compound represented by structural formula (I):

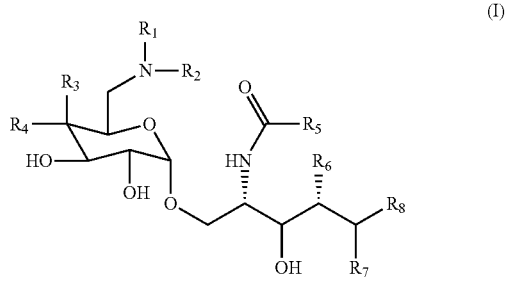

where $R_1$, $R_2$, $R_3$, $R_4$, $R_5$, $R_6$, $R_7$ and $R_8$ are defined herein below.

In another aspect, the invention provides a compound, termed "PBS-57," represented by structural formula (II)

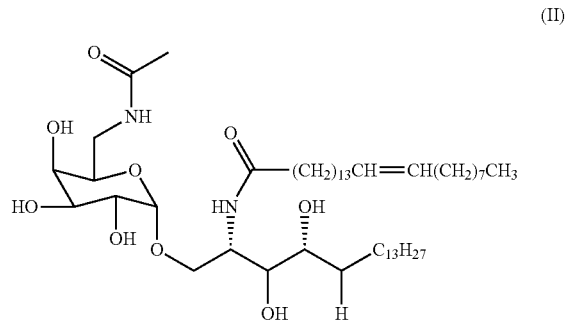

In another aspect, the invention provides a method of activating an NKT cell comprising contacting the NKT cell with the compound of formula (I) in the presence of a CD1d monomer or tetramer.

In yet another aspect, the invention provides a method of stimulating an immune response in a subject. The method includes a step of administering to the subject an effective amount of the compound of formula (I). Alternatively, the method of stimulating an immune response in a subject comprises a step of administering to the subject a population of NKT cells activated by contacting the NKT cells with the compound of formula (I) in the presence of a CD1 molecule. As a third alternative, the method of stimulating an immune response in a subject comprises administering to the subject a population of CD1+ antigen presenting cells contacted with the compound of formula (I).

In yet another aspect, the invention provides a composition comprising a compound of formula (I) and a physiologically acceptable vehicle.

In a further aspect, the invention provides a method of labeling an NKT cell in a medium comprising steps of complexing a compound of formula (I) with a CD1d tetramer to form a complex, contacting the complex with the NKT cell, removing the unbound complex from the medium, and detecting the complex.

DETAILED DESCRIPTION OF SEVERAL EMBODIMENTS

Figure 1:
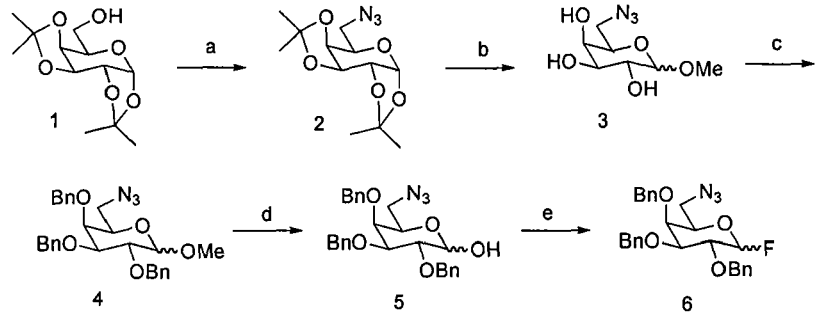
FIGS. 1A, 1B and 1C depict a suitable synthetic scheme for PBS-57.
Figure 1:
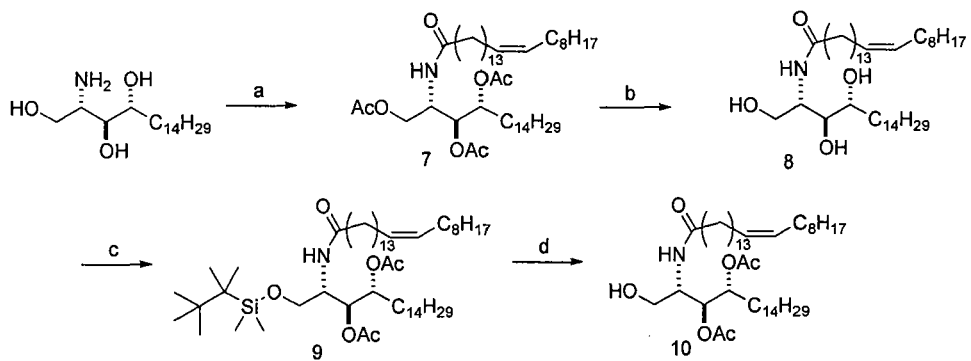
Figure 1:
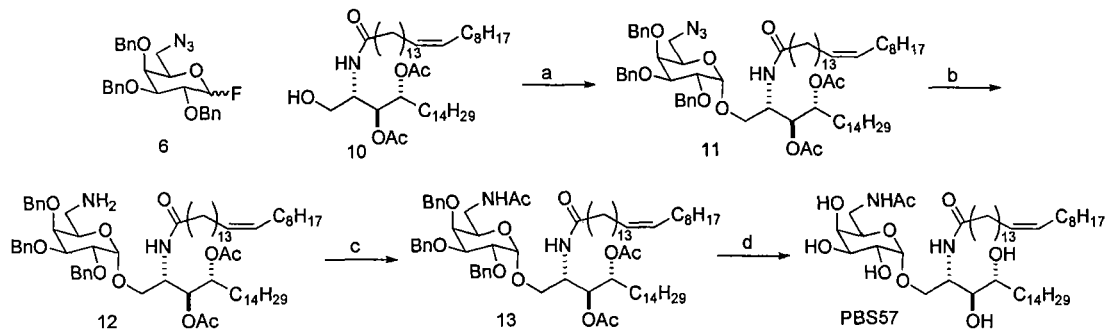
Figure 2:
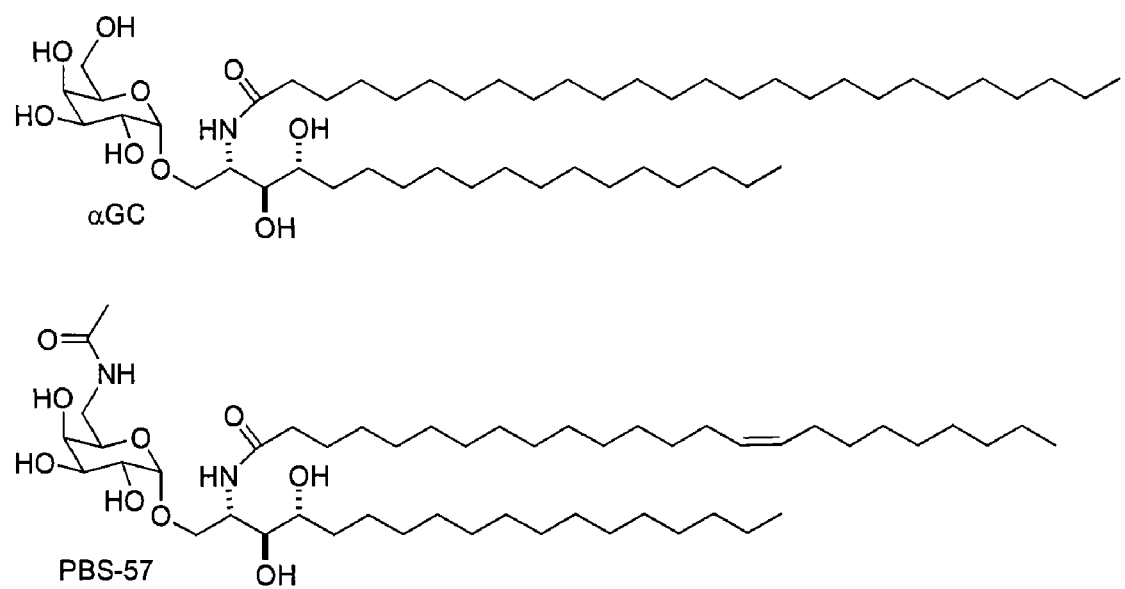
FIG. 2 depicts the structures of a prototypical compound of the invention, termed "PBS-57," and KRN7000.

In an effort to find compounds that activate NKT cells, the inventors have synthesized and studied a series of modified α-galactosyl ceramides ("αGCs"). As a result of this work, it was determined that one suitable modification to αGC is an addition of a cis-double bond in the acyl chain in the ceramide portion of the fatty acid. This modification was shown to increase solubility over fully saturated compounds and facilitate loading of the glycolipid into the CD1d binding site. A further suitable modification replaces the hydroxyl group at the C6 position of galactose in αGC with an amide linked to a small molecule. These modifications were found to yield compounds that retain the ability to stimulate cytokine release by NKT cells at levels comparable to KRN7000.

A prototypical compound of the invention, PBS-57 (shown in FIG. 1), which includes the above-described modifications, stains mouse and human NKT cells as well as KRN7000 and displays relatively high solubility. In vitro and in vivo studies of the NKT cell stimulating properties of PBS-57 indicated that it stimulates NKT cells more effectively than KRN7000.

Compounds

Compounds of the invention are glycolipids represented by formula I, shown below:

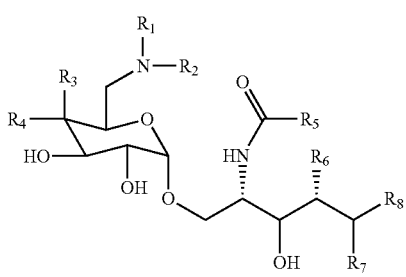

(I)

wherein:
$R_1$ is selected from:
  (i) $C(O)R_{13}$;
  (ii) $C(R_{13})R_{14}$, wherein $R_{14}$ is —H, or $R_{13}$ or $R_{14}$ and $R_2$ taken together form a double bond between the carbon and nitrogen atoms to which they are attached; or
  (iii) $SO_2R_{13}$;
    wherein $R_{13}$ is halo; hydroxy, $OR_9$; $OR_{10}$; amino, $NHR_9$; $N(R_9)_2$; $NHR_{10}$; $N(R_{10})_2$; aralkylamino; or C1-C12 alkyl optionally substituted with halo, hydroxyl, oxo, nitro, $OR_9$, $OR_{10}$, acyloxy, amino, $NHR_9$, $N(R_9)_2$, $NHR_{10}$, $N(R_{10})_2$, aralkylamino, mercapto, thioalkoxy, $S(O)R_9$, $S(O)R_{10}$, $SO_2R_9$, $SO_2R_{10}$, $NHSO_2R_9$, $NHSO_2R_{10}$, sulfate, phosphate, cyano, carboxyl, $C(O)R_9$, $C(O)R_{10}$, $C(O)OR_9$, $C(O)NH_2$, $C(O)NHR_9$, $C(O)N(R_9)_2$, $C_3$-$C_{10}$ cycloalkyl containing 0-3 $R_{11}$, $C_3$-$C_{10}$ heterocycyl containing 0-3 $R_{11}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{12}$, or heteroaryl containing 0-3 $R_{12}$; or $C_3$-$C_{10}$ cycloalkyl, $C_3$-$C_{10}$ heterocyclyl, $C_5$-$C_{10}$ cycloalkenyl, or $C_5$-$C_{10}$ heterocycloalkenyl optionally substituted with one or more halo hydroxyl, oxo, $OR_9$, $OR_{10}$, acyloxy, nitro, amino, $NHR_9$, $N(R_9)_2$, $NHR_{10}$, $N(R_{10})_2$, aralkylamino, mercapto, thioalkoxy, $S(O)R_9$, $S(O)R_{10}$, $SO_2R_9$, $SO_2R_{10}$, $NHSO_2R_9$, $NHSO_2R_{10}$, sulfate, phosphate, cyano, carboxyl, $C(O)R_9$, $C(O)R_{10}$, $C(O)OR_9$, $C(O)NH_2$, $C(O)NHR_{10}$, $C(O)N(R_{10})_2$, alkyl, haloalkyl, $C_3$-$C_{10}$ cycloalkyl containing 0-3 $R_{11}$, $C_3$-$C_{10}$ heterocyclyl containing 0-3 $R_{11}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl heteroaryl containing 0-3 $R_{12}$, or $C_6$-$C_{20}$ heteroaryl containing 0-3 $R_{12}$; or $C_2$-$C_6$ alkenyl, $C_2$-$C_6$ alkynyl, aryl, or heteroaryl optionally substituted with one or more halo, hydroxyl, $OR_9$, $OR_{10}$, acyloxy, nitro, amino, $NHR_9$, $N(R_9)_2$, $NHR_{10}$, $N(R_{10})_2$, aralkylamino, mercapto, thioalkoxy, $S(O)R_9$, $S(O)R_{10}$, $SO_2R_9$, $SO_2R_{10}$, $NHSO_2R_{10}$, sulfate, phosphate, cyano, carboxyl, $C(O)R_9$, $C(O)R_{10}$, $C(O)OR_9$, $C(O)NH_2$, $C(O)NHR_9$, $C(O)N(R_9)_2$, alkyl, haloalkyl, $C_3$-$C_{10}$ cycloalkyl containing 0-3 $R_{11}$, $C_3$-$C_{10}$ heterocycyl containing 0-3 $R_{11}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{12}$, or $C_6$-$C_{20}$ heteroaryl containing 0-3 $R_{12}$;

$R_2$ is —H or $C_1$-$C_6$ alkyl;
$R_3$ is —H if $R_4$ is —OH, or $R_3$ is —OH if $R_4$ is —H;
$R_4$ is —H if $R_3$ is —OH, or $R_4$ is —OH if $R_3$ is —H;
$R_5$ is selected from:
  (i) —$(CH_2)_x CH=CH(CH_2)_y CH_3$; or
  (ii) —$(CH_2)_x CH=CH(CH_2)_y CH=CH(CH_2)_z CH_3$,
    wherein X, Y and Z are integers independently selected from 1 to about 14;
$R_6$ is —OH or forms a double bond with $R_7$;
$R_7$ is —H or forms a double bond with $R_6$;
$R_8$ is a saturated or unsaturated hydrocarbon having from about 5 to about 15 carbon atoms;
each $R_9$ is independently a $C_1$-$C_{20}$ alkyl optionally substituted with halo, hydroxyl, alkoxy, amino, alkylamino, dialkylamino, sulfate, or phosphate;
each $R_{10}$ is independently an aryl optionally substituted with halo, haloalkyl, hydroxy, alkoxy, nitro, amino, alkylamino, dialkylamino, sulfate, or phosphate;
each $R_{11}$ is independently halo, haloalkyl, hydroxy, alkoxy, oxo, amino, alkylamino, dialkylamino, sulfate, or phosphate; and
each $R_{12}$ is independently halo, haloalkyl, hydroxy, alkoxy, nitro, amino, alkylamino, dialkylamino, sulfate, or phosphate.

Figure 8:
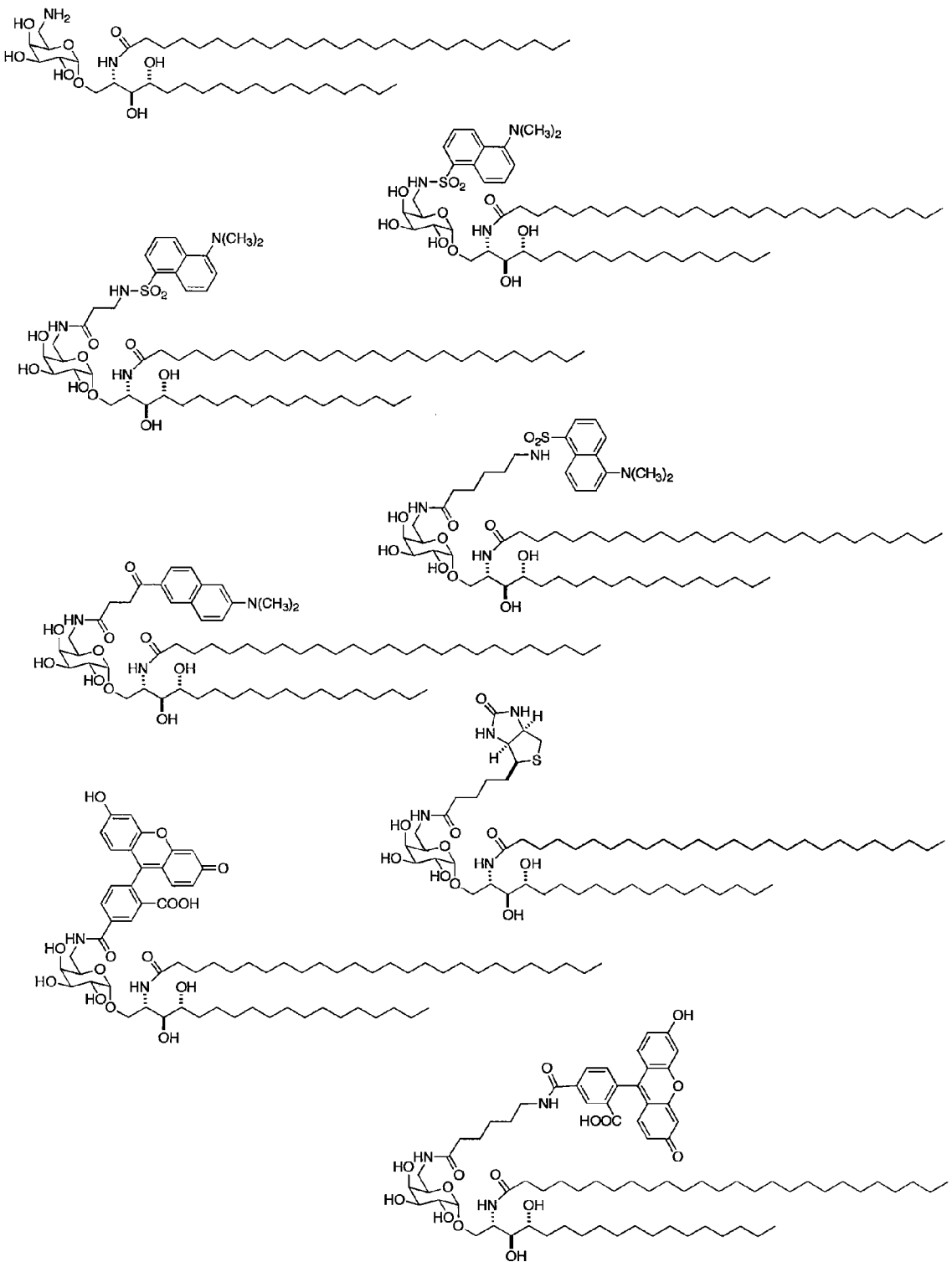
FIG. 8 shows structures for several suitable embodiments of compounds of the invention.
Figure 8:
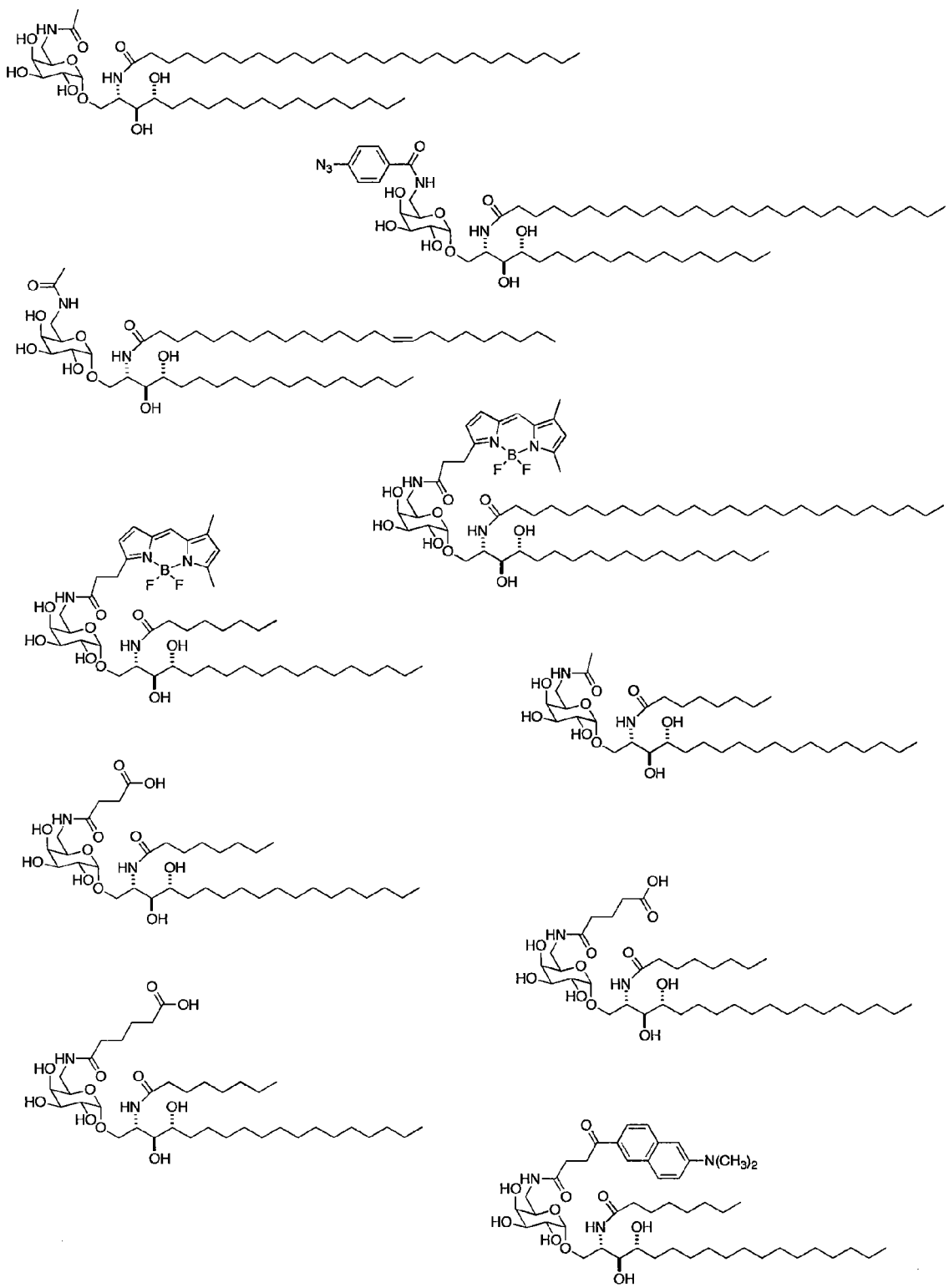
Figure 8:
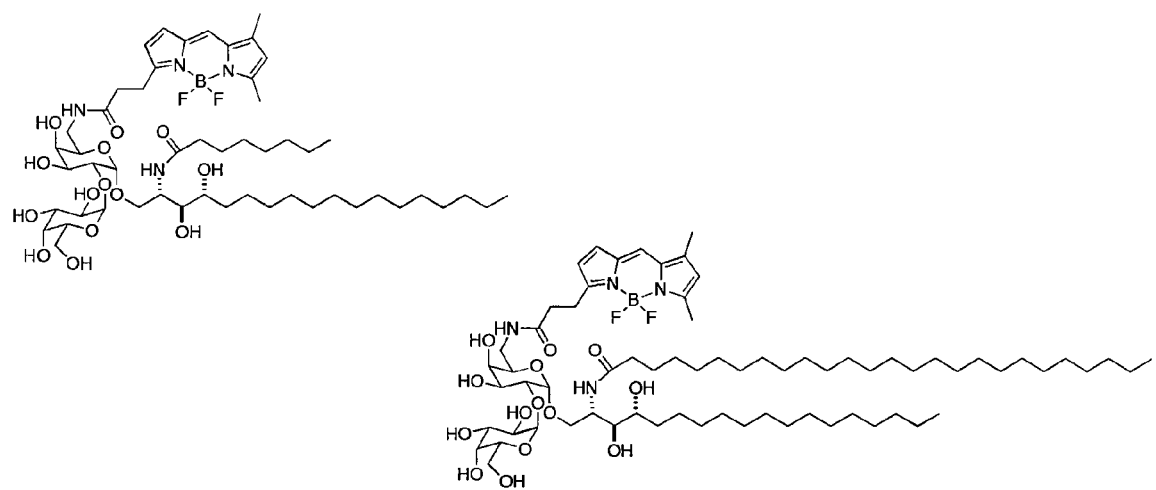

In particular embodiments of compounds of formula I, $R_5$ is (i), X is 13 and Y is 7. In other suitable embodiments, $R_1$ is —$CH_3$. In still other embodiments, $R_1$ is (i) and $R_{13}$ is —$CH_3$; $R_5$ is (i), and X is 13 and Y is 7; $R_6$ is —OH; $R_7$ is —H; and $R_8$ is. In further embodiments, if $R_1$ is (i) then $R_{13}$ is not —$CH_3$; if $R_5$ is (i), then x and y are not 13 and 7, respectively; $R_6$ is not —OH; $R_7$ is not —H; and $R_8$ is not $C_{13}H^{27}$. Structures for several suitable examples of compounds of the invention are shown in FIG. 8.

Terms used in the above description of glycolipids of the invention are defined as follows:

The term "glycolipid" refers to any compound containing one or more monosaccharide residues ("glyco" portion) bound by a glycosidic linkage to a hydrophobic moiety such as an acylglycerol, a sphingoid, a ceramide (N-acylsphingoid) or a prenyl phosphate ("lipid" portion). In particular embodiments, one or more saccharides are bound to a ceramide moiety.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The terms "arylarkyl" or "aralkyl" refer to an alkyl moiety in which an alkyl hydrogen atom is replaced by an aryl group, for example benzyl or 9-fluorenyl groups. The term "alkylamino" and "dialkylamino" refer to —NH(alkyl) and —NH(alkyl)$_2$ radicals respectively. The term "alkoxy" refers to an —O-alkyl radical. The term "mercapto" refers to an SH radical. The term "thioalkoxy" refers to an —S-alkyl radical.

The term "aryl" refers to an aromatic moncyclic, bicyclic, or tricyclic hydrocarbon ring system, wherein any ring atom capable of substitution can be substituted by a substituent, such as, but not limited to, phenyl, naphthyl, and anthracenyl.

The term "cycloalkyl" as employed herein includes saturated cyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclohexyl and adamantyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom capable of substitution can be substituted by a substituent. Examples of cycloalkyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$aryl (where n is 0-2), $S(O)_n$heteroaryl (where n is 0-2), $S(O)_n$heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof, unsubstituted aryl, unsubstituted heteroaryl, unsubstituted heterocyclyl, and unsubstituted cycloalkyl. In one aspect, the substituents on a group are independently any one single, or any subset of the aforementioned substituents.

One particularly suitable glycolipid of the invention, designated "PBS-57," is represented by structural formula II:

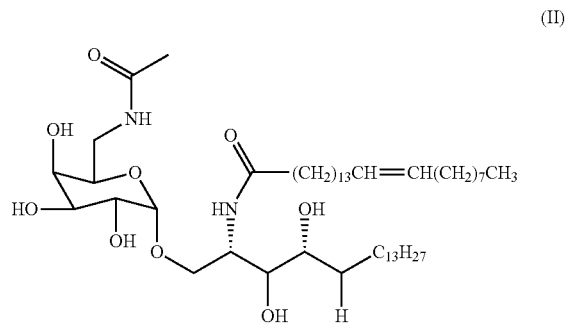

(II)

As with most glycolipids, solubility issues are central to handling the compounds. Compounds are usually solubilized in DMSO, and then diluted to working concentrations in aqueous solutions. The present compounds have been shown to be more soluble in DMSO than KRN7000, thereby giving low residual concentrations of DMSO in the working solutions. In suitable embodiments, the compounds of the invention are at least about 10 mg/mL in DMSO under ambient conditions (approximately 20° C.). In more suitable embodiments, the compounds of the invention are at least about 20 mg/mL in DMSO at ambient temperature. In further suitable embodiments, the compounds of the invention are at least 80%, at least two-fold, or at least 4-fold relative to the solubility of KRN7000 in DMSO at ambient temperature.

In particular embodiments, compounds of the invention are capable of binding a CD1d monomer or tetramer. The CD1d monomer may be soluble, immobilized on a solid surface, or expressed on the surface of an NKT cell. CD1d tetramers are well known and commercially available. As used herein, "capable of binding a CD1d monomer or tetramer" means the ability of the compound to bind CD1d in a lipid binding assay, i.e., a competition assay of a charged glycolipid and an uncharged control and resolution of glycolipid-loaded CD1 molecules by IEF (isoelectric focusing) electrophoresis, as described in Cantu et al., The Paradox of Immune Molecular Recognition of α-Galactosylceramide: Low Affinity, Low Specificity for CD1d, High Affinity for αβTCRs, Journal of Immunology, 2003, 170:p. 4673-4682, the disclosure of which is incorporated herein by reference. As determined by IEF, binding of the compound to CD1d molecules can be quantified relative to binding of an uncharged glycolipid to CD1d molecules. Compound binding to CD1d can be titrated to saturation and quantified from the IEF gels to determine equilibrium binding constants. A compound will be considered capable of binding a CD1d molecule if it displays a $K_D$ less than 1 mM when determined using the assay in Cantu et al. cited above.

Other methods for assessing the ability of a compound to bind a CD1d monomer or tetramer are known and include, e.g., gel filtration chromatography, gel electrophoresis, surface plasmon resonance and ELISA. Binding may also be assessed by staining NKT cells with compounds complexed to CD1d tetramers, as described in Liu, Y. et al., *J. Immun. Methods* 2006, 312: 34-39, incorporated herein by reference.

Using any suitable assay, the ability of a compound to bind to the CD1d molecules may be compared to the binding capabilities of KRN7000. Suitably, the compound exhibits at least 80% of the CD1d binding capability of KRN7000, more preferably at least 90%, more preferably at least two fold, more preferably at least four-fold of the CD1d binding capability of KRN7000.

In other embodiments, compounds of the invention are capable of activating an NKT cell. Activation of NKT cells can be assessed, e.g., as described in the below and in the examples.

Methods of Activating NKT Cells

"Stimulating an NKT cell" and "activating an NKT cell" are used interchangeably herein to refer to inducing an observable effect in an NKT cell that is consistent with a cellular response to engagement of the TCR of the NKT cell with an antigen presented in the context of CD1d molecule. Observable effects of activation of NKT cells include secretion of cytokines, clonal proliferation and upregulation of expression of cell surface markers, for example, CD69 molecules, IL-12 receptors and/or CD40L molecules. To activate an NKT cell in accordance with the present methods, the NKT cell is contacted with a compound of the invention in the presence of a CD1d monomer or tetramer. Suitably, a compound of the invention stimulates an NKT cell when the compound is complexed with, or bound to, a CD1d monomer or tetramer. Activation of the NKT cell results from contacting the TCR of the NKT cell with the complex, thereby eliciting an observable response, such as, e.g., altered cytokine expression. "A T cell receptor of an NKT cell", as the term is used herein, refers to the conserved, semi-invariant TCR of NKT cells comprising e.g., Vα14-Jα18/Vβ11 in humans and Vα14-Jα18/Vβ8 in mice.

As used herein, "contacting an NKT cell" refers to the in vitro addition of a compound of the invention to NKT cells in culture, optionally in the presence of immobilized, soluble, or insoluble CD1d monomers or tetramers or antigen presenting cells (APCs) expressing CD1d molecules, or to the in vivo administration of a compound of the invention to a subject. The compound may be presented to the TCR of the NKT cell by CD1d molecules on the surface of an antigen presenting cell (APC), such as a dendritic cell (DC) or macrophage. Alternatively, CD1d molecules may be plated and the NKT cells and a compound of the invention can be added to the CD1d molecules in vitro.

Examples of cytokines that may be secreted by NKT cells activated in accordance with the invention may include, but are not limited to, IL-10, IL-4, and IL-12, IL-13, GM-CSF, IFN-γ, IL-2, IL-1, IL-6, IL-8, TNF-α, and TGF-β. It is appreciated that combinations of any of the above-noted cytokines may be secreted by NKT cells upon activation. Methods for detecting and measuring levels of secreted cytokines are well-known in the art. As will be appreciated, assessing NKT cell activation is suitably accomplished by measuring cytokine expression by the NKT cell relative to a a suitable control.

NKT cell proliferation may also be induced by contacting NKT cells with one or more compounds of the invention. Proliferation is suitably measured in vitro by standard methods, e.g. $^3$H-thymidine or BrdU incorporation assays.

Upregulation of cell surface markers is also suitably observed upon activation of NKT cells. For example, CD69, CD25, CD40L and IL-12 receptors are upregulated upon activation of NKT cells. Immunologic methods, such as FACS, may be used to detect upregulation of cell surface markers, as well as other methods commonly employed in the art. Downstream effects of NKT cell activation, such as induction of DC maturation, are also observable, e.g., by measuring upregulation of CD80 and/or CD86 on DCs.

In vivo and ex vivo activation of NKT cells is specifically contemplated in addition to in vitro activation. Presentation of compounds of the invention to NKT cells in the context of CD1d molecules results in NKT cell activation and dendritic cell maturation. Consequently, these compounds stimulate immune responses against nominal antigens as well as infectious agents and neoplastic malignancies, including solid and hematologic tumors. Both cellular and humoral immunity may be stimulated by administering NKT cell agonist compounds, as further described below.

Methods of stimulating an NKT cell in vivo, i.e., in a subject, include administering a NKT cell agonist compound to the subject. Administration to a subject in accordance with some methods of the invention may include first formulating the NKT cell agonist compound with a physiologically acceptable vehicle and/or excipient to provide desired dosages, stability, etc. Suitable formulations for vaccine preparations and therapeutic compounds are known in the art. Methods of stimulating an NKT cell ex vivo may include use of adoptive transfer methods based on administering cells that have been contacted with NKT cell agonist compounds ex vivo to stimulate NKT cells in a subject. In some embodiments, the cells may be NKT cells that are stimulated ex vivo and injected into a subject. In other embodiments, the cells may be APCs that have been contacted with compounds of the invention ex vivo to allow loading of the surface-expressed CD1d molecules with the compound for presentation to NKT cells. The ex vivo stimulated NKT cells or loaded APCs can then be administered, e.g., by injection into the subject.

Methods of Stimulating an Immune Response

Some embodiments of the invention provide a method of stimulating an immune response in a subject. A "subject" is a vertebrate, suitably a mammal, more suitably a human. As will be appreciated, for purposes of study, the subject is suitably an animal model, e.g., a mouse. "Stimulating an immune response" includes, but is not limited to, inducing a therapeutic or prophylactic effect that is mediated by the immune system of the subject. More specifically, stimulating an immune response in the context of the invention refers to eliciting an NKT cell response in a subject by administering an effective amount of a compound of the invention to the subject, thereby inducing downstream effects such as production of antibodies, antibody heavy chain class switching, maturation of APCs, and stimulation of cytolytic T cells, T helper cells and both T and B memory cells. Alternatively, stimulation of an immune response in a subject may be accomplished by administering to the subject a population of NKT cells that have been activated as described above or a population of CD1d+ antigen presenting cells that have been contacted with a compound of the invention. Additionally, any combination of the above methods of stimulating an immune response may be suitable.

In some embodiments, the immune response stimulated according to the invention may be an antimicrobial immune response. Such an immune response suitably promotes clearance of an infectious agent or permits immune control of the agent such that disease symptoms are reduced or resolved, e.g., a persistent or latent infection.

In other embodiments, the enhanced immune response may be an anticancer or antitumor immune response. Such an immune response suitably promotes tumor rejection, reduces tumor volume, reduces tumor burden, prevents metastasis, and/or prevents recurrence of the tumor. The tumor may be any solid or hematologic tumor, including but not limited to leukemia, lymphoma, AIDS-related cancers, cancers of the bone, brain, breast, gastrointestinal system, endocrine system, eye, genitourinary tract, germ cells, reproductive organs, head and neck, musculoskeletal system, skin, nervous system or respiratory system. As is appreciated in the art, a cancer-specific immune response may be monitored by several methods, including: 1) measuring cytotoxicity of effector cells, using, e.g., a chromium release assay; 2) measuring cytokine secretion by effector cells; 3) evaluating T cell receptor (TCR) specificities, e.g., by using MHC-peptide multimers; 4) measuring the clonal composition of the T cell response; and/or 5) measuring T cell degranulation.

An enhanced immune response is also suitably assessed by the assays such as, e.g. activation of NKT cells, inducing cytokine production, inducing maturation of APCs, enhancing cytolytic and helper T cell functions, enhancing CD8+ and CD4+ T cell recruitment, enhancing antibody production, inducing antibody class switching and breaking tolerance.

Stimulating an immune response in a subject in accordance with the invention may be accomplished by administering to the subject a composition including a compound of the invention and in some embodiments, an antigen. The compound and the antigen may or may not induce a detectably enhanced immune response when administered to a subject independently.

Suitably, the compound and the antigen are co-administered to stimulate an immune response in a subject. The term "co-administration" is meant to refer to any administration protocol in which a compound of the invention and an antigen are administered to a subject. The compound and the antigen may be in the same dosage formulations or separate formulations. Where the compound and antigen are in separate dosage formulations, they can be administered concurrently, simultaneously or sequentially (i.e., administration of one may directly follow administration of the other or they may be given episodically, i.e., one can be given at one time followed by the other at a later time, e.g., within a week), as long as they are given in a manner sufficient to allow both to achieve therapeutically or prophylactically effective amounts in the subject. The compound and the antigen may also be administered by different routes, e.g., one may be administered intravenously while the second is administered intramuscularly, intravenously or orally.

In some embodiments, the compound is suitably added to a vaccine composition or is co-administered with a vaccine composition. Addition of a compound of the invention to a vaccine composition or co-administration with a vaccine composition may be particularly suitable in cases where the antigen has a low rate of efficacy as a vaccine and/or must be administered in an amount or at a dose greater than what might be considered ideal due to side effects, cost and/or availability of the antigen, etc. Examples of such vaccines may include, but are not limited to human papillomavirus vaccines, acute otitis media vaccine (PREVNAR®), influenza vaccines, cholera vaccines and the telomerase cancer vaccine.

Administration to a subject may be carried out by any suitable method, including intraperitoneal, intravenous, intramuscular, subcutaneous, transcutaneous, oral, nasopharyngeal or transmucosal absorption, among others. Suitably, a compound of the invention is administered in an amount effective to activate an NKT cell or cells such that a prophylactic or therapeutic effect is achieved in the subject, e.g., an antitumor immune response or antimicrobial immune response.

Administration to a subject also includes use of adoptive transfer methods based on administering cells that have been contacted with a compound of the invention ex vivo to stimulate or enhance an immune response in a subject. In some embodiments, the cells may be NKT cells that are activated ex vivo and injected into a subject to provide or enhance an immune response to, e.g., cancerous cells or infectious agents. In some embodiments, the cells may be APCs that have been contacted with a compound of the invention ex vivo to allow complexing with the CD1d molecules expressed by the APC. Antigen presenting cells can then be administered, e.g., by injection into the subject, to provide a suitable immune response. This method of administration allows for stimulation of the immune response with minimal exposure of the subject or the subject's cells to the compounds.

Administration of compounds of the invention to a subject in accordance with the invention appears to exhibit beneficial effects in a dose-dependent manner. Thus, within broad limits, administration of larger quantities of the compounds is expected to activate greater numbers of NKT cells or activate NKT cells to a greater degree than does administration of a smaller amount. Moreover, efficacy is also contemplated at dosages below the level at which toxicity is seen.

It will be appreciated that the specific dosage administered in any given case will be adjusted in accordance with the compound or compounds being administered, the disease to be treated or prevented, the condition of the subject, and other relevant medical factors that may modify the activity of the compound or the response of the subject, as is well known by those skilled in the art. For example, the specific dose for a particular patient depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compound of the invention and of a known agent such as αGalCer, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. It is anticipated that dosages of the compound in accordance with the present invention will prevent or reduce symptoms at least 50% compared to pre-treatment symptoms. It is specifically contemplated that vaccine preparations and compositions of the invention may palliate or alleviate symptoms of the disease without providing a cure, or, in some embodiments, may be used to cure or prevent the disease or disorder.

Suitable effective dosage amounts for administering the compounds may be determined by those of skill in the art, but typically range from about 1 microgram to about 10,000 micrograms per kilogram of body weight weekly, although they are typically about 1,000 micrograms or less per kilogram of body weight weekly. In some embodiments, the effective dosage amount ranges from about 10 to about 5,000 micrograms per kilogram of body weight weekly. In another embodiment, the effective dosage amount ranges from about 50 to about 1,000 micrograms per kilogram of body weight weekly. In another embodiment, the effective dosage amount ranges from about 75 to about 500 micrograms per kilogram of body weight weekly. The effective dosage amounts described herein refer to total amounts administered, that is, if more than one compound is administered, the effective dosage amounts correspond to the total amount administered. The compound can be administered as a single weekly dose or as divided doses.

In some embodiments, a tumor antigen and the compound are co-administered to a subject to induce an anti-tumor immune response in the subject. Suitably, co-administration of the antigen with the compound enhances the anti-tumor response and results in inhibition of tumor growth, reduction in tumor burden and treatment of cancer, as described above.

Compositions

The compounds of the invention, as described above, are suitably included in a composition with a physiologically acceptable vehicle. A "physiologically acceptable" vehicle is any vehicle that is suitable for in vivo administration (e.g., oral, transdermal or parenteral administration) or in vitro use, i.e., cell culture. Suitable physiologically acceptable vehicles for in vivo administration include water, buffered solutions and glucose solutions, among others. A suitable vehicle for cell culture is commercially available cell media. Additional components of the compositions may suitably include excipients such as stabilizers, preservatives, diluents, emulsifiers or lubricants, in addition to the physiologically acceptable vehicle and one or more compounds of the invention. In particular, suitable excipients include, but are not limited to, Tween 20, DMSO, sucrose, L-histadine, polysorbate 20 and serum.

Suitably, compositions comprising compounds of the invention may be formulated for in vivo use, i.e., therapeutic or prophylactic administration to a subject. In some embodiments, the compositions are formulated for parenteral administration. A suitable dosage form for parenteral administration is an injectable. An injectable dosage form may be an isotonic solution or suspension and may be prepared using a suitable dispersion agent, wetting agent or suspension agent, as known in the art. In other embodiments, the compositions are formulated for oral administration. Suitable oral dosage forms include tablets, capsules, syrups, troches and wafers, among others. Oral dosage formulations suitably include lactose, starch, cellulose derivatives, magnesium stearate, stearic acid, glycols, and others. It will be appreciated that the compositions of the invention are not limited to any particular exemplified dosage form, but can be formulated in any manner described in the art, for example, in Remington's Pharmaceutical Sciences, Mack Publishing Co., (2000), which is incorporated herein by reference.

In addition to the compound of the invention and a physiologically acceptable vehicle, some embodiments of the invention further include CD1d monomers or tetramers. In these compositions, at least a portion of the compound present in the composition is bound to at least a portion of the CD1d monomers or tetramers. Optionally, amounts of CD1d molecules and concentration of the compound of the invention can be optimized such that substantially all of the CD1d molecules in the composition are bound by compound of the invention.

In further embodiments, the compound of the invention (or the compound bound by a CD1d monomer or tetramer) and an antigen and are suitably co-formulated in a composition. Antigens included in the composition may be polypeptide or carbohydrate moieties, or combinations thereof, for example, glycoproteins. The antigen may be derived from an infectious agent (e.g., a pathogenic microorganism), a tumor, an endogenous molecule (e.g., a "self" molecule), or, for purposes of study, a nominal antigen, such as ovalbumin. The composition may be also by formulated as a vaccine using a variety of preparative methods known to those of skill in the art. See Remington's Pharmaceutical Sciences, Mack Publishing Co., (2000), which is incorporated herein by reference.

In some embodiments, antigens for inclusion in compositions of the invention are suitably derived from attenuated or killed infectious agents. It will be understood that whole microorganisms or portions thereof (e.g., membrane ghosts; crude membrane preparations, lysates and other preparations of microorganisms) may suitably be included as an antigen. Suitable infectious agents from which an antigen may be derived include, but are not limited to, pathogenic viruses and microorganisms. In some contexts, suitable antigens are obtained or derived from a viral pathogen that is associated with human disease including, but not limited to, HIV/AIDS (Retroviridae, e.g., gp120 molecules for HIV-1 and HIV-2 isolates, HTLV-1, HTLV-11), influenza viruses (Orthomyxoviridae, e.g., types A, B and C), herpes (e.g., herpes simplex viruses, HSV-1 and HSV-2 glycoproteins gB, gD and gH), rotavirus infections (Reoviridae), respiratory infections (parainfluenza and respiratory syncytial viruses), Poliomyelitis (Picornaviridae, e.g., polioviruses, rhinoviruses), measles and mumps (Paramyxoviridae), Rubella (Togaviridae, e.g., rubella virus), hepatitis (e.g., hepatitis viruses types A, B, C, D, E and/or G), cytomegalovirus (e.g., gB and gH), gastroenteritis (Caliciviridae), Yellow and West Nile fever (Flaviviridae), Rabies (Rhabdoviridae), Korean hemorrhagic fever (Bunyaviridae), Venezuelan fever (Arenaviridae), warts (Papillomavirus), simian immunodeficiency virus, encephalitis virus, varicella zoster virus, Epstein-Barr virus, and other virus families, including Coronaviridae, Birnaviridae and Filoviridae.

Suitable bacterial and parasitic antigens can also be obtained or derived from known bacterial agents responsible for diseases including, but not limited to, diphtheria, pertussis, tetanus, tuberculosis, bacterial or fungal pneumonia, otitis media, gonorrhea, cholera, typhoid, meningitis, mononucleosis, plague, shigellosis or salmonellosis, Legionnaires' disease, Lyme disease, leprosy, malaria, hookworm, Onchocerciasis, Schistosomiasis, Trypanosomiasis, Leishmaniasis, giardiases, amoebiasis, filariasis, *Borrelia*, and trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Specific pathogens from which antigens can be derived include *M. tuberculosis, Chlamydia, N. gonorrhoeae, Shigella, Salmonella, Vibrio cholerae, Treponema pallidum, Pseudomonas, Bordetella pertussis, Brucella, Francisella tularensis, Helicobacter pylori, Leptospira interrogans, Legionella pneumophila, Yersinia pestis, Streptococcus* (types A and B), pneumococcus, meningococcus, *Haemophilus influenza* (type b), *Toxoplasma gondii, Moraxella catarrhalis*, donovanosis, and actinomycosis; fungal pathogens include candidiasis and aspergillosis; parasitic pathogens include *Taenia*, flukes, roundworms, amebiasis, giardiasis, *Cryptosporidium, Schistosoma, Pneumocystis carinii*, trichomoniasis and trichinosis. The present invention can also be used to provide a suitable immune response against numerous veterinary diseases, such as foot-and-mouth diseases, coronavirus, *Pasteurella multocida, Helicobacter, Strongylus vulgaris, Actinobacillus pleuropneumonia*, Bovine Viral Diarrhea Virus (BVDV), *Klebsiella pneumoniae, E. coli*, and *Bordetella pertussis*, parapertussis and brochiseptica.

In some embodiments, antigens for inclusion in compositions of the invention are suitably tumor-derived antigens or autologous or allogeneic whole tumor cells. Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include cdk4 (melanoma), β-catenin (melanoma), caspase-8 (squamous cell carcinoma), MAGE-1 and MAGE-3 (melanoma, breast, glioma), tyrosinase (melanoma), surface lg idiotype (e.g., BCR) (lymphoma), Her-2/neu (breast, ovarian), MUC-1 (breast, pancreatic) and HPV E6 and E7 (cervical carcinoma). Additional suitable tumor antigens include prostate specific antigen (PSA), sialyl Tn (STn), heat shock proteins and associated tumor peptides (e.g., gp96), ganglioside molecules (e.g., GM2, GD2, and GD3), Carcinoembryonic antigen (CEA) and MART-1.

Labeling NKT Cells

In another embodiment, the invention provides a method for labeling NKT cells in a medium. The method can be used to identify NKT cells in a medium from other cell types. In a first step, a compound of the invention is complexed to soluble CD1d tetramer. The tetramer is suitably labeled. A "label," as used herein, is any entity that can be assayed. Suitable labels include, but are not limited to strepavidin, biotin and fluorophores, such as, e.g., PE or FITC. The NKT cells are labeled by contact with the labeled compound/CD1d tetramer complex in a suitable medium. A suitable medium may be phosphate buffered saline (PBS) or commercially available cell medium, as known in the art. Unbound glycolipid/tetramer complexes may be removed from media by any means known in the art, e.g. washing and centrifugation of the cells and removal of medium. Cells labeled with the complex may be detected by any suitable means known in the art, such as flow cytometry or fluorescence microscopy.

The following examples are provided to assist in a further understanding of the invention. The particular materials and conditions employed are intended to be further illustrative of the invention and are not limiting upon the reasonable scope thereof.

EXAMPLES

Example 1

PBS-57 Synthesis and Solubility

PBS-57 was synthesized as shown in FIG. 1. Reagents corresponding to FIG. 1A are as follows (yields in parentheses): (a) $PPh_3$, DPPA, DIAD (79%). (b) AcCl, MeOH (81%). (c) BnBr, NaH, DMF (47%). (d) AcOH, HCl (69% yield). (e) DAST, $CH_2Cl_2$ (87%). Reagents corresponding to FIG. 1B are as follows (yields in parentheses): (a) Nervonic acid, DCC, NHS, THF; $Ac_2O$, $Et_3N$, DMAP, (48%). (b) MeONa, MeOH, (71%). (c) Dimethylthexylsilyl chloride, pyridine; $Ac_2O$, DMAP, (80%). (d) THF, HF, (83%). Reagents corresponding to FIG. 1C are as follows (yields in parentheses): (a) $AgClO_4$, $SnCl_2$, $CH_2Cl_2$, (56%). b) $PPh_3/H_2O$, THF. c) $Ac_2O$, Pyridine, DMAP, (80% overall) (d) Na°, $NH_3$, −78° C. (47%).

The preparation of the intermediates in the synthetic route shown in FIG. 1 are described below.

Preparation of 2: Compound 1 (3.00 g, 11.3 mmol) was dissolved in dry THF (20 mL), cooled to 0° C., and $PPh_3$ (5.95 g, 22.6 mmol) was added to the solution, followed by DIAD (5 mL, 22.6 mmol), then DPPA (3.7 ml, 22.6 mmol). The mixture was allowed warm to room temperature and stir overnight. The mixture was concentrated under reduce pressure, then dissolved in EtOAc (200 ml), washed with 5% HCl (80 ml), continued to washed it with saturated $NaHCO_3$, the extracts were concentrated in vacuo, and the product was purified by column chromatography ($SiO_2$, 1:5 EtOAc:hexanes) giving a clear glass (2.61 g, 79% yield). NMR ($^1$H, $CDCl_3$) d 5.55 (d, J=5.0 Hz, 1 H), 4.63 (dd, J=2.5, 8.0 Hz, 1 H), 4.34 (dd, J=2.5, 5.0 Hz, 1 H), 4.20 (dd, J=2.0, 8.0 Hz, 1 H), 3.93-3.90 (m, 1 H), 3.51 (dd, J=9.0, 12.5 Hz, 1 H), 3.36 (dd, J=5.5, 13.0 Hz, 1 H), 1.55 (s, 3 H), 1.46 (s, 3 H), 1.34 (s, 3 H); $^{13}$C NMR (500 Hz, $CDCl_3$) d 109.8, 108.9, 96.5, 77.2, 77.0, 67.17, 50.8, 26.2, 26.1, 25.1, 24.6.

Preparation of 4: Compound 2 (3.71 g, 13.0 mmol) was dissolved in MeOH (40 mL), cooled to 0° C., and AcCl (8.6 mL) was added. The mixture was allowed warm to room temperature and stirred overnight. The solvent was removed under reduced pressure, and the residue was purified by chromatography ($SiO_2$, 10% MeOH in $CH_2Cl_2$) yielding 3 (as mixture of anomers) as a white solid (2.31 g, 81% yield). To a solution of 3 (1.5 g, 6.9 mmol) in DMF (60 mL) was added sodium hydride in oil (1.26 g, 60% in mineral oil). The mixture was stirred for 5 min at 0° C., then benzyl bromide (4.9 mL, 41.4 mmol) was added dropwise. The stirring was continued for 12 h at room temperature, and then methanol (10 mL) was added. The solvent was removed in vacuo and the resulting solid was dissolved/suspended in $CH_2Cl_2$. The mixture was washed with 2 M HCl and water, dried ($Na_2SO_4$), and concentrated. Column chromatography (SiO2, EtOAc:hexanes 1:6) gave 4 as a clear glass (1.6 g, 47% yield). NMR ($^1$H, CDCl3) d 7.40-7.25 (m, 15 H), 5.02-4.62 (m, 7 H), 4.14-3.76 (m, 4 H), 3.57-3.48 (m, 1 H), 3.39 (s, 3 H), 2.94 (dd, J=2.4, 4.4 Hz, 1 H); NMR ($^{13}$C, CDCl3) d 138.65, 138.58, 138.34, 128.68, 128.61, 128.32, 128.12, 128.01, 127.87, 127.78, 99.01, 79.16, 76.48, 75.45, 74.81, 73.89, 69.98, 55.71, 51.64; HRFAB-MS (thioglycerol+$H^+$ matrix) m/e ($[M+H]^+$) 490.2347, calcd 490.2342.

Preparation of 5: Compound 4 (1.6 g, 3.2 mmol) was dissolved in acetic acid: 6 M HCl (50 mL: 7 mL). The mixture was stirred at 85° C. for 1 h, and the solution was concentrated under reduced pressure. The product was extracted with chloroform (100 mL) and washed with cold water (2×50 mL), and the combined extracts were dried over $Na_2SO_4$ and concentrated in vacuo. After chromatography (SiO2, EtOAc:hexanes 1:4), compound 5 (1.0 g, 69% yield) was obtained as a clear oil. NMR ($^1$H, CDCl3) d 7.39-7.28 (m, 15 H), 6.38 (d, J=3.5 Hz, 1 H), 5.02-4.58 (m, 6 H), 4.17 (dd, J=11.0, 4.0 Hz, 1 H), 3.91-3.88 (m, 3 H), 3.47 (dd, J=12.5, 7.0 Hz, 1 H), 3.15 (dd, J=12.5, 7.0 Hz, 1 H), 2.12 (s, 3 H); NMR ($^{13}$C, CDCl3) d 169.55, 138.59, 138.13, 138.00, 128.68, 128.62, 128.57, 128.56, 128.53, 128.51, 128.18, 128.13, 128.10, 128.03, 127.98, 127.85, 127.79, 127.60, 90.65, 78.67, 75.45, 75.31, 74.95, 74.69, 74.60, 74.42, 73.57, 73.53, 71.89, 50.85, 21.28; HRFAB-MS (thioglycerol+Na$^+$ matrix) m/e ([M+Na]$^+$) 540.2112 (100%), calcd 540.2111.

Preparation of 6: Compound 5 (3.09 g, 5.7 mmol.) was dissolved in 200 mL of $CH_2Cl_2$, followed by dropwise addition of DAST (0.906 mL). The solution was stirred at room temperature for 30 min before the reaction was quenched with $H_2O$ (30 mL). The mixture was then diluted with $CH_2Cl_2$ and washed with water and brine, the organic layer was dried and concentrated in vacuo. The desired product (2.7 g, 87% yield) was obtained as a clear oil after chromatography (SiO$_2$, EtOAc:hexanes 1:6). NMR ($^1$H, CDCl$_3$) d 7.40-7.25 (m, 15 H), 5.63 (dd, J=54.0, 2.5 Hz, 1 H), 5.00 (d, J=11.5 Hz, 1 H), 4.88-4.72 (m, 4 H), 4.61 (d, J=11.0 Hz, 1 H), 4.01-3.88 (m, 4 H), 3.51 (dd, J=12.5, 7.5 Hz, 1 H), 3.13 (dd, J=12.0, 6.0 Hz, 1H); NMR ($^{13}$C, CDCl$_3$) d 138.38, 138.09, 138.07, 128.74, 128.71, 128.66, 128.56, 128.23, 128.20, 128.16, 128.04, 127.80, 107.12, 105.32, 78.45, 75.85, 75.67, 74.99, 74.48, 73.99, 73.67, 72.14, 72.11, 50.96; HRFAB-MS (thioglycerol+Na$^+$ matrix) m/e ([M+Na]$^+$) 500.1956 (100%), calcd 500.1962.

Preparation of 8. Nervonic acid (3.0 g, 8.2 mmol) was dissolved in anhydrous THF (100 mL) at 5° C. followed by NHS (1.88 g, 16.3 mmol) and DCC (3.38 g, 16.3 mmol). The mixture was heated to reflux for 2 h. Phytosphingosine dissolved in THF and pyridine was added to the reaction mixture and refluxed for 12 h. Acetic anhydride (9 mL) was added followed by triethylamine (9 mL), DMAP (300 mg), and the mixture was stirred for 2 h. The solvent was removed in vacuo. Triacetate 7 (3.4 g, 48.6% yield) was isolated by chromatography (SiO$_2$, EtOAc:Hexane 1:8). Sodium metal (230 mg, 10 mmol) was added to MeOH (100 mL). Triacetate 7 (3.4 g, 4.4 mmol) was added, and the mixture was stirred for 1 h then centrifuged (3000 rpm, 5 m) to give a white solid. The supernatant was removed, and the solid rinsed with fresh MeOH (80 mL) to remove any remaining base. After removal of the supernatant, the crude white solid (2.1 g, 71%) was dried under vacuo. NMR ($^1$H, CDCl$_3$) d 6.14 (d, J=9.5, 1 H), 5.34 (m, 2 H), 5.12 (dd, J=3, 8.5 Hz, 1 H), 4.93 (m, 1 H), 4.50 (m, 1 H), 4.29 (dd, J=5, 11.5 Hz, 1 H), 4.0 (dd, J=3.0, 11.5 Hz, 1 H), 2.21 (t, J=7.5 Hz, 2 H), 2.08 (s, 3 H), 2.05-1.99 (m, 10 H), 1.66-1.60 (m, 4 H), 1.33-1.22 (m, 56 H), 0.89 (t, J=7.0 Hz, 6 H); NMR ($^{13}$C, CDCl$_3$) d 178.25, 173.19, 171.31, 170.99, 170.20, 129.99, 73.15, 71.92, 63.05, 60.52, 47.50, 36.81, 34.11, 32.05, 29.91, 29.83, 29.80, 29.74, 29.67, 29.51, 29.45, 29.39, 29.26, 28.10, 27.33, 25.80, 25.68, 24.92, 22.82, 21.13, 20.88, 20.84, 14.30, 14.24. HRFAB-MS (thioglycerol+Na$^+$ matrix) m/e ([M+Na]$^+$) 814.6526, calcd 814.6537.

Preparation of 10. Triol 8 (2.1 g, 3.09 mmol) was dissolved in pyridine (15 mL), and dimethylthexylsilyl chloride (0.606 ml, 3.09 mmol) was added. After 5 min, acetic anhydride (1.16 mL, 12.3 mmol), and DMAP (200 mg) were added, and the mixture was stirred for 2 h. Purification by chromatography (SiO2, EtOAc:Hex 1:20) yielded 9 (2.0 g, 80% yield) as a clear oil. Compound 9 (2.0 g, 2.4 mmol) was dissolved in THF (5 mL) in a centrifuge tube (plastic), followed by adding aqueous HF (5 mL). After completion of the reaction, the mixture was pour into saturated NaHCO$_3$ (80 mL), then extracted with EtOAc (100 mL×2). The organic layer was dried and concentrated, then purified by chromatography (SiO2, EtOAc:Hexane 1:2) to afford 10 as white solid (1.5 g, 83%). ($^1$H, CDCl$_3$) d 6.66 (d, J=9.0 Hz, 1 H), 5.34 (t, J=4.0 Hz, 1 H), 5.10 (dd, J=2.0, 9.0 Hz, 1 H), 4.95-4.92 (m, 1 H), 4.20-4.14 (m, 1 H), 3.61-3.55 (m, 2 H), 2.22 (t, J=8.0 Hz, 2 H), 2.13 (s, 3 H), 2.04-1.99 (m, 7 H), 1.66-1.60 (m, 4 H), 1.34-1.22 (m, 56 H), 0.89-0.86 (m, 6 H). NMR ($^{13}$C, CDCl3) d 173.44, 171.52, 171.45, 130.08, 73.54, 72.49, 61.61, 49.74, 36.93, 32.15, 32.13, 29.94, 29.90, 29.84, 29.78, 29.76, 29.64, 29.56, 27.87, 27.42, 25.97, 25.93, 22.91, 21.27, 21.09, 14, 36. HRFAB-MS (thioglycerol+Na$^+$ matrix) m/e ([M+Na]$^+$) 772.6429, calcd 772.6431.

Preparation of 11. Compound 6 (112 mg, 0.21 mmol) and compound 10 (75 mg, 0.10 mmol) were dissolved in $CH_2Cl_2$ (15 mL), and powdered 4 Å molecular sieves (900 mg) were added. The mixture was cooled to 0° C., stirred for 10 min, and AgClO$_4$ (62 mg, 0.30 mmol) and SnCl$_2$ (57 mg, 0.30 mmol) were introduced. The mixture was allowed to warm to room temperature with stirring over 3 h, then filtered through celite and washed with $CH_2Cl_2$. The combined filtrate was concentrated under reduced pressure. The residue was purified by chromatography (SiO$_2$, EtOAc:hexanes 1:7) to give 11 (68 mg, 56% yield). NMR ($^1$H, CDCl3) d 7.42-7.19 (m, 15 H), 6.67 (d, J=9.5 Hz, 1 H), 5.37-5.33 (m, 2 H), 5.24-5.22 (m, 1 H), 4.98 (dd, J=11.0 Hz, 3.0, 1 H), 4.93 (dt, J=10.5 Hz, 3.0 Hz, 1 H), 4.86-4.55 (m, 6 H), 4.37-4.31 (m, 1 H), 4.03 (dd, J=10.5 Hz, 3.0 Hz, 1 H), 3.92-3.77 (m, 4 H), 3.60-3.56 (m, 2 H), 3.05 (dd, J=4.5 Hz, 12.5 Hz, 1 H), 2.14 (t, J=8.0 Hz, 2 H), 2.06-2.00 (m, 10 H), 1.67-1.59 (m, 4 H), 1.38-1.25 (m, 56 H), 0.91-0.87 (m, 6 H); NMR ($^{13}$C, CDCl3) d 173.20, 171.22, 170.38, 138.76, 138.40, 138.23, 130.14, 128.78, 128.67, 128.36, 128.23, 128.11, 127.85, 127.67, 100.81, 78.73, 75.01, 74.90, 73.71, 73, 42, 71.64, 70.59, 60.80, 51.50, 48.40, 36.96, 32.16, 29.96, 29.68, 29.57, 27.75, 27.46, 25, 96, 25, 88, 22.94, 21.26, 21.17, 14.38; HRFAB-MS (thioglycerol+Na$^+$ matrix) m/e ([M+Na]$^+$) 1229.8448, calcd 1229.8433.

Preparation of 12. To a solution of 11 (68 mg, 0.056 mmol) in THF (3 mL), was added H$_2$O (0.6 ml) and triphenylphosphine (23 mg, 0.085 mmol). The reaction mixture was stirred at room temperature overnight. The solution was concentrated under reduced pressure. The residue was dissolved THF (5 mL) and Ac$_2$O (0.1 ml), Et$_3$N (0.1 mL), and DMAP (5 mg) were added. The mixture was stirred for 2 h. The solution was concentrated, and column chromatography gave 13 (55 mg, 80% yield). NMR ($^1$H, CDCl$_3$) d 7.41-7.27 (m, 15 H), 6.73 (d, J=10.0 Hz, 1 H), 6.12 (t, J=6.5 Hz, 1 H), 5.36-5.34 (m, 2 H), 5.24 (dd, J=3.0 Hz, 13.5 Hz, 1 H), 4.96 (d, J=11.5 Hz, 1 H), 4.86 (tt, J=10.5, 3.0 Hz, 1 H), 4.82-4.65 (m, 6 H), 4.38 (tt, J=3.0, 9.5 Hz, 1 H), 4.04 (dd, J=3.0, 10.5 Hz, 1 H), 3.93 (dd, J=3.0, 11.5 Hz, 1 H), 3.87-3.78 (m, 3 H), 3.53-3.46 (m, 2 H), 3.32-3.27 (m, 1 H), 2.13 (t, J=8.0 Hz, 2 H), 2.06-2.00 (m, 10 H), 1.88 (s, 3 H), 1.72-1.1.57 (m, 4 H), 1.38-1.22 (m, 56 H), 0.90-0.87 (m, 6 H); NMR ($^{13}$C, CDCl$_3$) d 173.49, 171.74, 170.51, 170.40, 138.89, 138.64, 138.56, 130.13, 129.21, 128.65, 128.31, 128.11, 127.77, 100.91, 79.14, 76.64, 74.91, 73.84, 73.64, 71.32, 71.10, 70.27, 48.68, 40.24, 36.84, 32.14, 29.94, 29.90, 29.86, 29.82, 29.76, 29.68, 29.60, 29.55, 27.89, 27.45, 25.94, 25.79, 23.37, 22.92, 21.41, 21.19, 14.35; HRFAB-MS (thioglycerol+Na$^+$ matrix) m/e ([M+Na]$^+$) 1245.8634, calcd 1245.8633.

Preparation of PBS57. Na° (21 mg, 0.91 mmol) was added to liquid NH$_3$ (20 ml) under N$_2$ at −78° C., and the mixture was stirred for 5 min. Compound 13 (55 mg, 0.045 mmol) was dissolved in dry THF (2 mL). The solution was added to the blue liquid NH$_3$ and stirred for 2 h. The reaction was quenched with MeOH. After the ammonia was removed, the solution was concentrated, and column chromatography gave PBS57 (18 mg, 47%). NMR ($^1$H, 10% MeOD in CDCl$_3$), d 5.35 (t, J=5.0 Hz, 2H), 4.87 (d, J=3.0 Hz, 1 H), 4.16-4.13 (m, 1 H), 3.85-3.51 (m, 9 H), 3.24-3.21 (m, 1 H), 2.1 (t, J=7.5 Hz, 2 H), 2.03-1.98 (m, 7 H), 1.64-1.52 (m, 4 H), 1.38-1.22 (m, 56 H), 0.89-0.86 (m, 6 H); NMR ($^{13}$C, 10% MeOD in CDCl$_3$) d 174.61, 172.60, 129.96, 99.57, 74.71, 72.16, 69.92, 69.12, 68.88, 67.14, 50.53, 49.48, 49.30, 49.13, 48.96, 48.79, 48.62, 39.70, 36.58, 32.70, 31.97, 29.83, 29.77, 29.65, 29.56, 29.50, 29.45, 29.42, 29.39, 29.36, 27.25, 25.95, 25.91, 22.72, 22.58, 14.10; HRFAB-MS (thioglycerol+Na$^+$ matrix) m/e ([M+Na]$^+$) 891.7014, calcd 891.7014.

The solubility of KRN7000 in DMSO is <5 mg/mL while the solubility of PBS-57 in DMSO was 20 mg/mL (22.4 mM).

Example 2

Staining of Vα14i NKT Cells with PBS-57 Loaded CD1d Tetramers

An typical means to isolate and quantify CD1 responsive NKT cells is through flow cytometry using fluorophore tagged CD1d tetramers loaded with sphingoglycolipids. To test for the ability of PBS-57 to facilitate CD1d tetramer staining, glycolipid-loaded CD1d tetramers were formed. Biotinylated mouse sCD1d molecules (in PBS) were mixed with PBS-57 or KRN7000 at a molar ratio of 1:3 (protein:lipid) and incubated overnight at room temperature. The following day, 80 μg of streptavidin-PE (Pharmagen) was added to 200 μg of the CD1-glycolipid mix and incubated at room temperature for 4 hours. Tetramers were stored at 4° C. until use.

Figure 3:
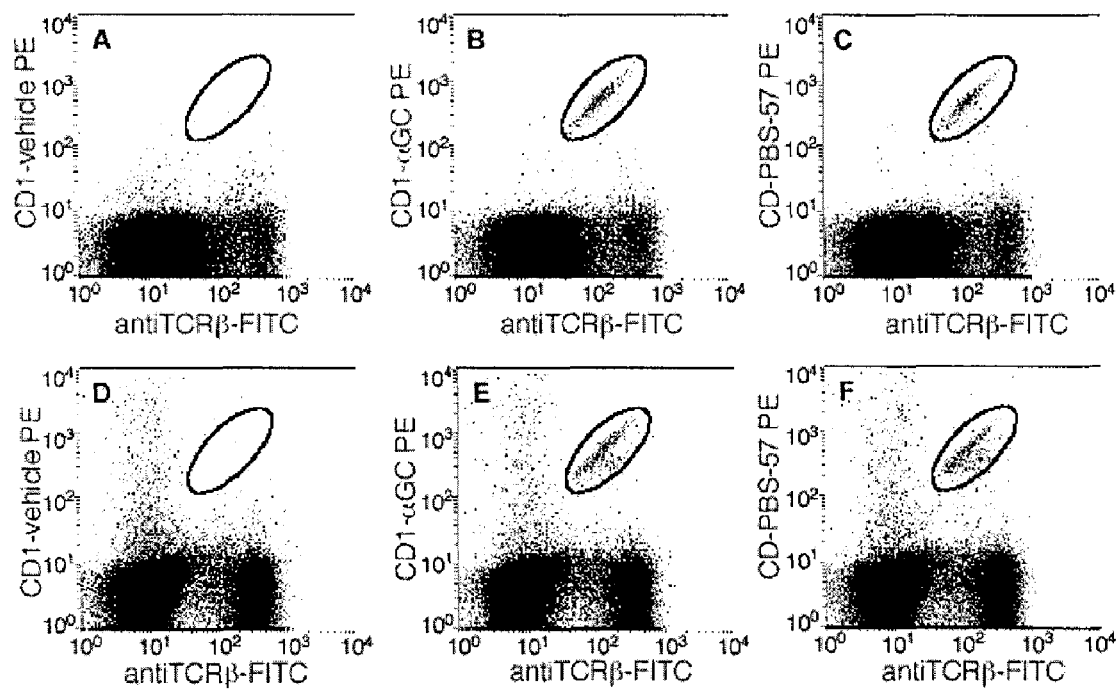
FIG. 3 depicts staining of Vα14iNKT cells from a mouse thymus (A-C) and spleen (D-F) cell populations with anti-TCRβ-FITC and either PBS-57 (C and F), KRN7000 (B and E) or vehicle alone (A and D).

Single cell suspensions of thymocytes and splenocytes were isolated from C57BL/6J mice (Jackson Laboratories, Bar Harbor, Me.) as known in the art. The TCR repertoire of the NKT cells was limited with an invariable $V_\alpha$ subunit ($V_\alpha$14 in mice) and varied $V_\beta$ subunits. $10^6$ cells were incubated with 200 μL staining media (2% BSA, 1% NaN$_3$, 10 mM EDTA in PBS) with 2.4G2 (1:100; ATCC, Manassas, Va.) and Neutravidin (5 μg/200 μl; Molecular Probes, Eugene, Oreg.) for 20 minutes on ice. Cells were pelleted and resuspended in staining media with anti-TCRβ FITC (1:100; H57-597 BD-Pharmingen, San Deigo, Calif.) and CD1/glycolipid or vehicle (without glyclipid) loaded tetramers conjugated with streptavidin-PE (1:400) and incubated on ice for 45 minutes. Cells were washed twice in staining media, fixed with 1% paraformaldehyde in PBS and analyzed by flow cytometry. As seen in FIG. 3, PBS-57 stained NKT cells in the spleen and thymus similar to KRN7000.

Example 3

PBS-57 is Able to Facilitate Staining of Nkt Cells that Express a Wide Variety of $V_\beta$ TCR Subunits The TCR expressed on NKT cells are limited to a invariant $V_\alpha$, subunit, and a variable $V_\beta$ subunit that respond to glycolipid presentation by CD1d. To determine if PBS-57 loaded tetramers were $V_\beta$ subunit specific in their ability to bind, NKT cell hybridomas expressing different $V_\beta$ were tested for their ability to bind PBS-57 loaded CD1d tetramers. NKT hybridomas were established in the Bendelac and Hayakawa laboratories as described previously (Zhou et al., Lysosomal glycoshingolipid recognition by NKT cells, Science, 2004, 306:p. 1786-1788, and Gui et al., TCR beta chain influences but does not solely control autoreactivity of V alpha 14J281T cells, Journal of Immunology, 2001, 167:p. 6239-6246).

For staining of NKT cell hybridomas, soluble CD1d (sCD1d) tetramers were loaded with PBS-57 or KRN7000 by the following procedure. Stock reagents of the following were prepared: sCD1d (1 mg/ml in phosphate buffer saline (PBS)); PBS-57 (1 mg/ml in DMSO); Tween 20 (0.5% in PBS); and streptavidin-APC (80 μg/mL in PBS). 10 μL sCD1d stock, 1 μL PBS-57 stock, and 10 μL Tween 20 stock were mixed, and 79 μL PBS was added to bring the volume up to 100 μL. The solution was incubated at 37° C. for 3 hours. To separate unbound glycolipid, the mixture was applied to a Microcon YM30 filter (Millipore) that has been previously wetted with PBS (400 μL). The loaded membrane was centrifuged until only ~10 μL of solution remained. The volume was then increased to 100 μL by addition of PBS. The solution was agitated to aid in freeing the protein from the filter. The Microcon unit was inverted into a fresh Eppendorf tube and the contents were centrifuged into the tube. A 10 μL aliquot of the solution was removed and the streptavidin-APC solution (5 μL) was added. The resulting solution was incubated at 37° C. for 2 hours.

NKT cell hybridomas were suspended in PBS and streptavidin (1 μg/mL) to block surface biotin of cells for 20 minutes at room temperature. Unloaded sCD1d-streptavidin-cychrome was used to assess the non-specific binding of unloaded empty CD1d tetramers by incubation for 20 minutes at room temperature. Staining of NKT cells was preformed at 37° C. for 4 hours using the glycolipid-sCD1d-streptavidin-APC complex. The cells were washed by PBS and assayed via flow cytometry.

Figure 4:
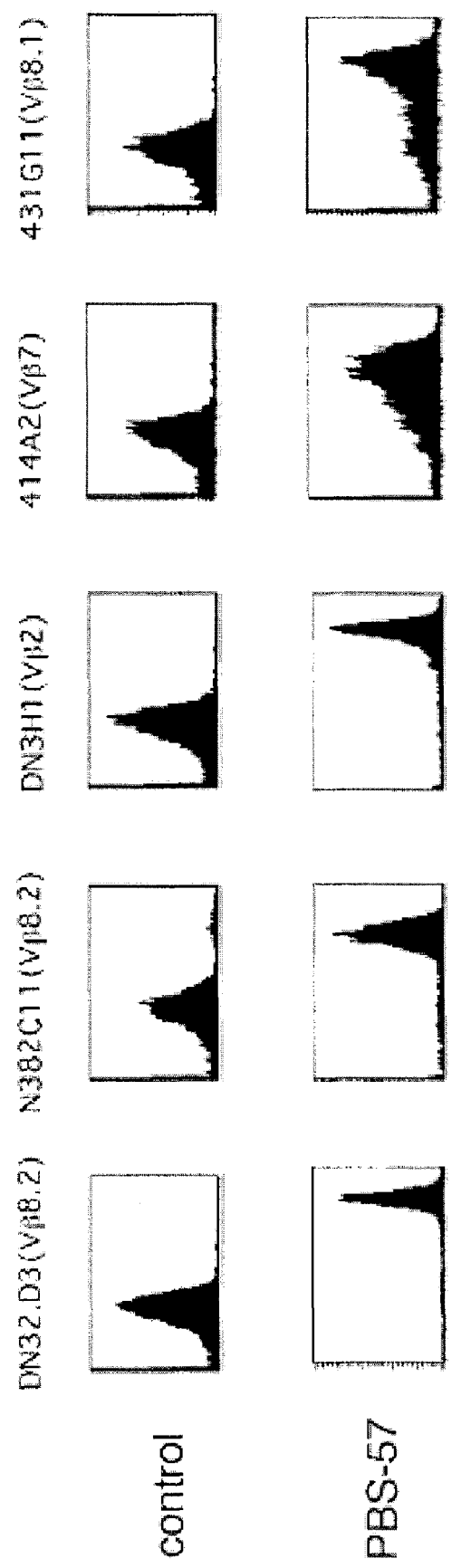
FIG. 4 depicts binding of PBS-57 loaded CD1d-tetramers to NKT hybridoma cell lines in the context of varying Vβ TCR expressed by the NKT cell. CD1d-tetramers loaded with a non-stimulating glycolipid (α-galactosycholesterol) was used as a negative control.

As seen in FIG. 4, variations in the $V_\beta$ subunit of the TCR on the NKT cell did not affect the binding of PBS-57 loaded CD1d tetramers, and thus PBS-57 may be a "universal" ligand for NKT cells.

Example 4

Figure 5:
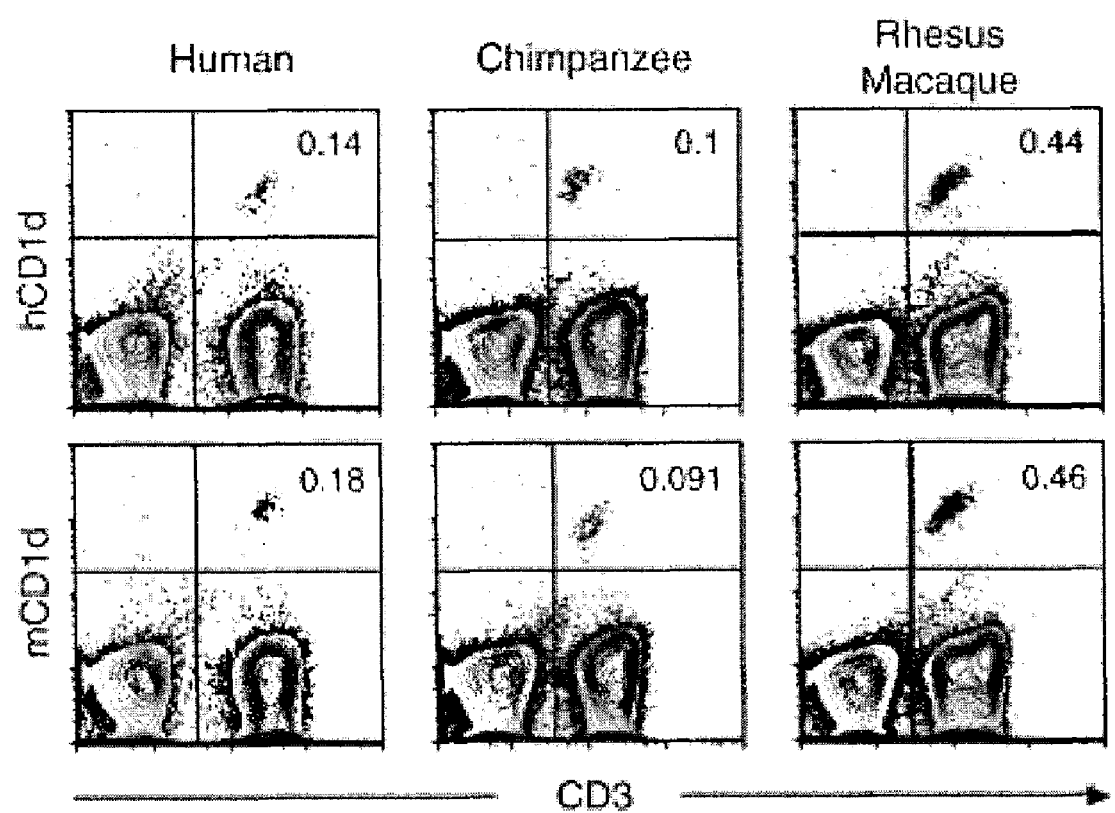
FIG. 5 depicts staining of CD1d-responsive NKT cells using PBS-57 loaded mouse and human CD1d-tetramers in human and non-human primate blood samples.

Ability of PBS-57 to Facilitate CD1d Tetramer Staining of NKT Cells in Human and Non-Human Primate Blood Samples To test whether PBS-57 could facilitate NKT cell binding in blood samples of both human and non-human primates, mouse and human CD1d tetramers were loaded with PBS-57 as described in Example 2. A majority of the human blood samples contained sufficient NKT cells (>0.08% of CD3-positive cells) to observe staining (14 out of 17 samples), while some samples may have contained too few NKT cells to allow detection of staining (Lee et al., 2002). Among the non-human primates, significant NKT cell staining was observed with a majority of chimpanzee blood samples (6 out of 10 samples) and one quarter of samples from rhesus macaques (12 samples). Representative dot plots of NKT cell staining in human, chimpanzee and rhesus macaques are shown in FIG. 5. No staining was seen in samples from pigtail macaques or sooty mangabeys, it may be due to the limited population of NKT cells circulating in the blood and the small sample size.

Example 5

Cytokine Release in Response to PBS-57/CD1d Tetramer Complex in Vitro

Figure 6:
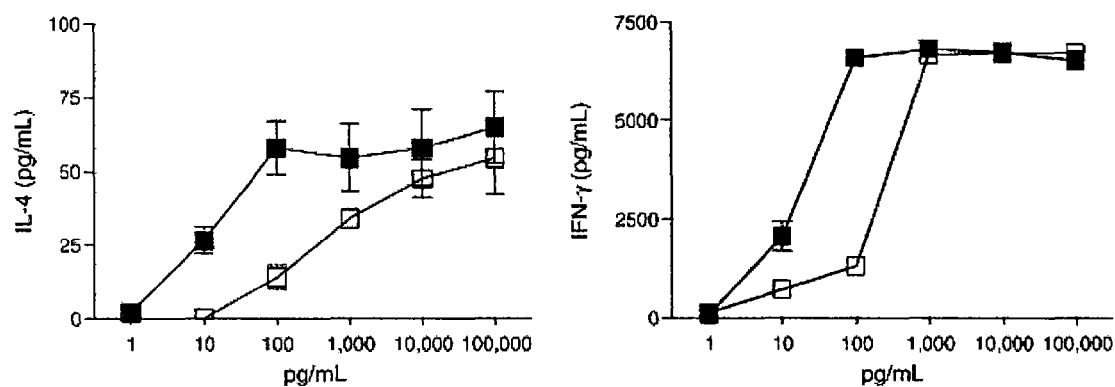
FIG. 6 depicts cytokine release from B6 mouse splenocytes stimulated with PBS-57 (black squares) or KNR7000 (white squares).

To determine if PBS-57 stimulated cytokine release by NKT cells in vitro, 5×10$^5$ mouse splenocytes isolated from B6 mice were incubated in separate wells with 10$^5$, 10$^4$, 10$^3$, 100, 10 and 1 pg/mL of PBS-57 or KRN7000 in RPMI 1640 media supplemented with 10% FBS, 50 μM 2-mercaptoethanol, 2 mM glutamine and antibiotics. After 48 hours, IL-4 and IFNγ levels were measured by ELISA (BD Pharmingen). As seen in FIG. 6, cytokine responses to PBS-57 plateau at approximately 100 pg/mL, as compared to 1000 pg/mL for KRN7000. PBS-57 was able to induce both Th1 and Th2 cytokine secretion.

Example 6

Cytokine Release in Response to PBS-57/CD1d Tetramer Complex in Vivo

Figure 7:
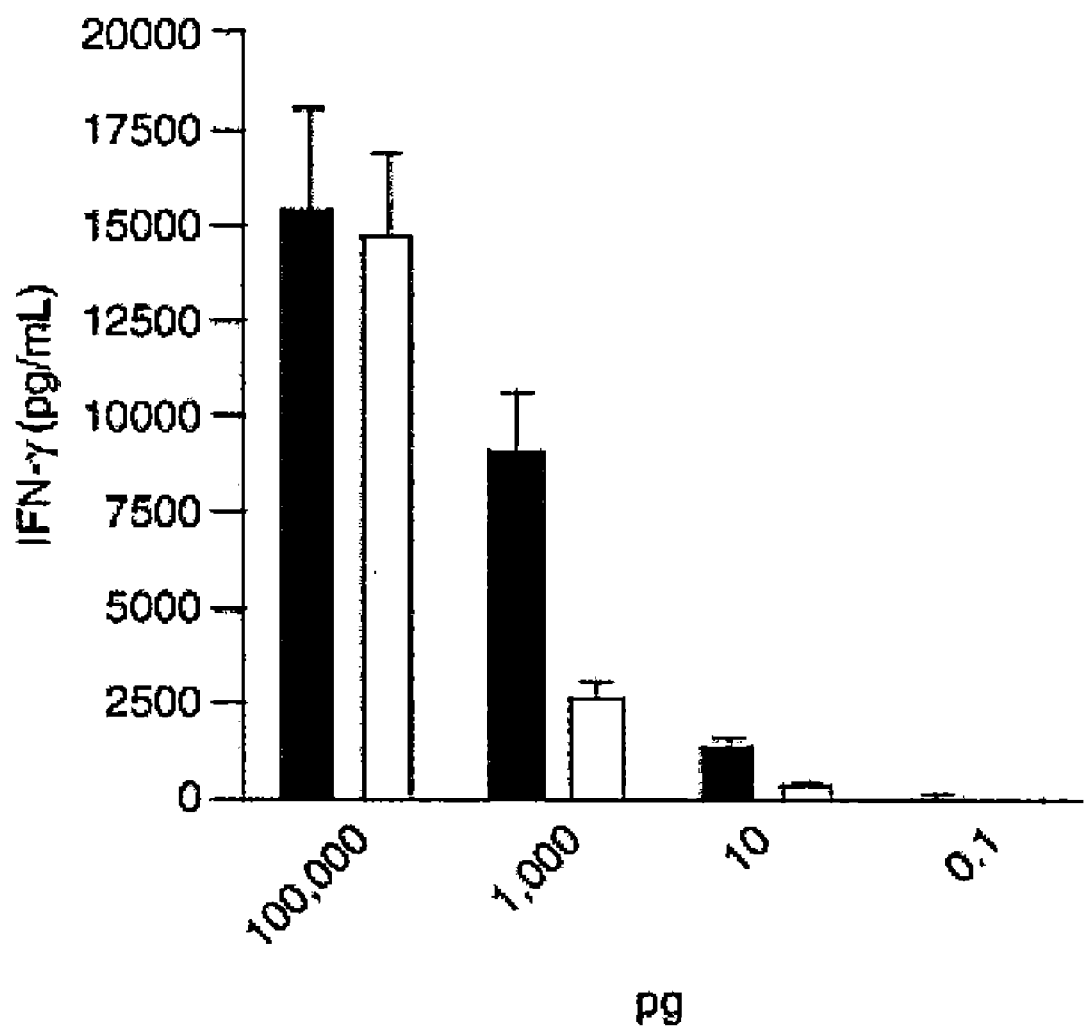
FIG. 7 depicts serum concentrations of INF-γ from mice intravenously injected with indicated quantities of PBS-57 (black bars) or KRN7000 (white bars) glycolipids.

To examine if PBS-57 elicited an immune response in vivo, the ability of PBS-57 and KRN7000 to elicit an increase in cytokine levels in a mouse was assayed. 1 mg/ml stock solutions of PBS-57 and KRN7000 in DMSO were prepared. The PBS-57 and KRN7000 solutions were diluted with PBS to 1, 100, $10^4$ and $10^6$ pg/mL. 100 μL of each solution was injected intravenously into 6 week-old B6 mice. Serum samples were isolated from the mice at 24 hours, and the concentration of INF-γ was assayed by ELISA (BD Pharmingen). FIG. 7 demonstrates the serum INF-γ concentrations, and PBS-57 appears to elicit cytokine level equal to or greater than KRN7000.

While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application.

We claim:

1. A compound represented by structural formula (I):

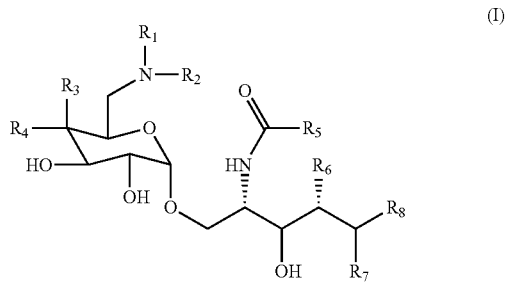

wherein:

R$_1$ is selected from:

(i) C(O)R$_{13}$; or (ii) SO$_2$R$_{13}$;

wherein R$_{13}$ is halo; hydroxy, OR$_9$; OR$_{10}$; amino, NHR$_9$; N(R$_9$)$_2$; NHR$_{10}$; N(R$_{10}$)$_2$; aralkylamino; or C$_1$-C$_{12}$ alkyl optionally substituted with halo, hydroxyl, oxo, nitro, OR$_9$, OR$_{10}$, acyloxy, amino, NHR$_9$, N(R$_9$)$_2$, NHR$_{10}$, N(R$_{10}$)$_2$, aralkylamino, mercapto, thioalkoxy, S(O)R$_9$, S(O)R$_{10}$, SO$_2$R$_9$, SO$_2$R$_{10}$, NHSO$_2$R$_9$, NHSO$_2$R$_{10}$, sulfate, phosphate, cyano, carboxyl, C(O)R$_9$, C(O)R$_{10}$, C(O)OR$_9$, C(O)NH$_2$, C(O)NHR$_9$, C(O)N(R$_9$)$_2$, C$_3$-C$_{10}$ cycloalkyl containing 0-3 R$_{11}$, C$_3$-C$_{10}$heterocycyl containing 0-3 R$_{11}$, C$_2$-C$_6$ alkenyl, C$_2$-C$_6$ alkynyl, C$_5$-C$_{10}$ cycloalkenyl, C$_5$-C$_{10}$ heterocycloalkenyl, C$_6$-C$_{20}$ aryl containing 0-3 R$_{12}$, or heteroaryl containing 0-3 R$_{12}$; or C$_3$-C$_{10}$ cycloalkyl, C$_3$-C$_{10}$ heterocyclyl, C$_5$-C$_{10}$ cycloalkenyl, or C$_5$-C$_{10}$ heterocycloalkenyl optionally substituted with one or more halo hydroxyl, oxo, OR$_9$, OR$_{10}$, acyloxy, nitro, amino, NHR$_9$, N(R$_9$)$_2$, NHR$_{10}$, N(R$_{10}$)$_2$, aralkylamino, mercapto, thioalkoxy, S(O)R$_9$, S(O)R$_{10}$, SO$_2$R$_9$, SO$_2$R$_{10}$, NHSO$_2$R$_9$, NHSO$_2$R$_{10}$, sulfate, phosphate, cyano, carboxyl, C(O)R$_9$, C(O)R$_{10}$, C(O)OR$_9$, C(O)NH$_2$, C(O)NHR$_{10}$, C(O)N(R$_{10}$)$_2$, alkyl, haloalkyl, C$_3$-C$_{10}$ cycloalkyl containing 0-3 R$_{11}$,C$_3$-C$_{10}$ heterocyclyl containing 0-3 R$_{11}$, C$_2$-C$_6$ alkenyl, C$_2$-C$_6$ alkynyl, C$_5$-C$_{10}$ cycloalkenyl, C$_5$-C$_{10}$ heterocycloalkenyl, C$_6$-C$_{20}$ aryl heteroaryl containing 0-3 R$_{12}$, or C$_6$-C$_{20}$ heteroaryl containing 0-3 R$_{12}$; or C$_2$-C$_6$ alkenyl, C$_2$-C$_6$ alkynyl, aryl, or heteroaryl optionally substituted with one or more halo, hydroxyl, OR$_9$, OR$_{10}$, acyloxy, nitro, amino, NHR$_9$, N(R$_9$)$_2$, NHR$_{10}$, N(R$_{10}$)$_2$, aralkylamino, mercapto, thioalkoxy, S(O)R$_9$, S(O)R$_{10}$, SO$_2$R$_9$, SO$_2$R$_{10}$, NHSO$_2$R$_{10}$, sulfate, phosphate, cyano, carboxyl, C(O)R$_9$, C(O)R$_{10}$, C(O)OR$_9$, C(O)NH$_2$, C(O)NHR$_9$, C(O)N(R$_9$)$_2$, alkyl, haloalkyl, C$_3$-C$_{10}$ cycloalkyl containing 0-3 R$_{11}$, C$_3$-C$_{10}$ heterocycyl containing 0-3 R$_{11}$, C$_2$-C$_6$ alkenyl, C$_2$-C$_6$ alkynyl, C$_5$-C$_{10}$ cycloalkenyl, C$_5$-C$_{10}$ heterocycloalkenyl, C$_6$-C$_{20}$ aryl containing 0-3 R$_{12}$, or C$_6$-C$_{20}$ heteroaryl containing 0-3 R$_{12}$;

R$_2$ is —H or C$_1$-C$_6$ alkyl;—

R$_3$ is —H if R$_4$ is —OH, or R$_3$ is —OH if R$_4$ is —H;

R$_4$ is —H if R$_3$ is —OH, or R$_4$ is —OH if R$_3$ is —H;

R₅ is selected from:
(i) —(CH₂)ₓCH═CH(CH₂)ᵧCH₃; or
(ii) —(CH₂)ₓCH═CH(CH₂)ᵧCH═CH(CH₂)_ZCH₃, wherein X, Y and Z are integers independently selected from 1 to about 14;

R₆ is —OH or forms a double bond with R₇;
R₇ is —H or forms a double bond with R₆;
R₈ is a saturated or unsaturated hydrocarbon having from about 5 to about 15 carbon atoms;
each R₉ is independently a C₁-C₂₀ alkyl optionally substituted with halo, hydroxyl, alkoxy, amino, alkylamino, dialkylamino, sulfate, or phosphate;
each R₁₀ is independently an aryl optionally substituted with halo, haloalkyl, hydroxy, alkoxy, nitro, amino, alkylamino, dialkylamino, sulfate, or phosphate;
each R₁₁ is independently halo, haloalkyl, hydroxy, alkoxy, oxo, amino, alkylamino, dialkylamino, sulfate, or phosphate; and
each R₁₂ is independently halo, haloalkyl, hydroxy, alkoxy, nitro, amino, alkylamino, dialkylamino, sulfate, or phosphate.

2. The compound of claim 1, wherein R₅ is (i), X is 13 and Y is 7.

3. The compound of claim 1, wherein R₁₃ is —CH₃.

4. The compound of claim 1, wherein:
R₁ is (i) and R₁₃ is —CH₃;
R₅ is (i), and X is 13, and Y is 7;
R₆ is —OH;
R₇ is —H; and
R₈ is C₁₃H₂₇.

5. The compound of claim 1 wherein:
if R₁ is (i) then R₁₃ is not —CH₃;
if R₅ is (i) then x and y are not 13 and 7, respectively;
R₆ is not —OH;
R₇ is not —H; and
R₈ is not C₁₃H₂₇.

6. A compound represented by structural formula (II)

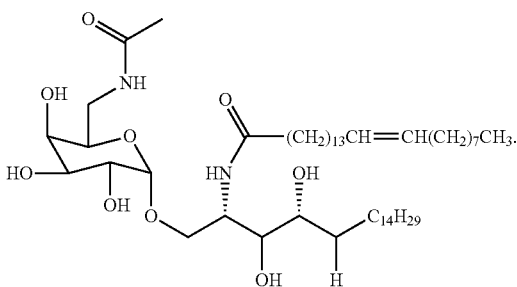

(II)

7. The compound of claim 1, wherein the solubility of the compound is at least about 20 mg/mL in DMSO.

8. The compound of claim 1, wherein the compound Is capable of binding a CD1d monomer or tetramer.

9. The compound of claim 1, wherein compound is capable of activating an NKT cell.

10. A composition comprising the compound of claim 1 and a physiologically acceptable vehicle.

11. The composition of claim 10, further comprising a CD1d monomer or tetramer, wherein the compound is bound to the CD1d monomer or tetramer.

12. The composition of claim 10, further comprising an antigen.

13. A method of activating an NKT cell comprising contacting the NKT cell with the compound of claim 9 in the presence of a CD1d monomer or tetramer.

14. The method of claim 13, wherein the compound is bound to the CD1d monomer or tetramer.

15. The method of claim 13, wherein the CD1d monomer or tetramer is soluble.

16. The method of claim 13, wherein the CD1d monomer is expressed on a cell surface.

17. The method of claim 16, wherein the cell is an antigen presenting cell.

18. The method of claim 13, wherein activation of the NKT cell is characterized by altered cytokine expression relative to a control.

19. The method of claim 13, wherein the NKT cell is activated in vitro.

20. The method of claim 13, wherein the NKT cell is activated in vivo.

21. A method of stimulating an immune response in a subject comprising administering to the subject an effective amount of: a) the compound of claim 1 wherein the compound is capable of activation an NKT cell; b) a population of NKT cells activated by contacting the cells with a compound according to a) in the presence of a CD1d monomer or tetramer; c) a population of CD1d+antigen presenting cells contacted with the compound of claim 1; or d) any combination of a), b) and c).

22. A method of labeling an NKT cell in a medium comprising:
a) complexing the compound of claim 9 with a CD1d tetramer to form a complex;
b) contacting the NKT cell with the complex;
c) removing unbound complex from the medium; and
d) detecting the complex.

23. The compound of claim 9, wherein:
R₁ is C(O)R₁₃ and R₁₃ is —CH₃;
R₅ is —(CH₂)ₓCH═CH(CH₂)ᵧCH₃, and X is 13 and Y is 7;
R₆ is —OH;
R₇ is —H; and
R₈ is C₁₃H₂₇.

24. The composition of claim 10, wherein the compound is

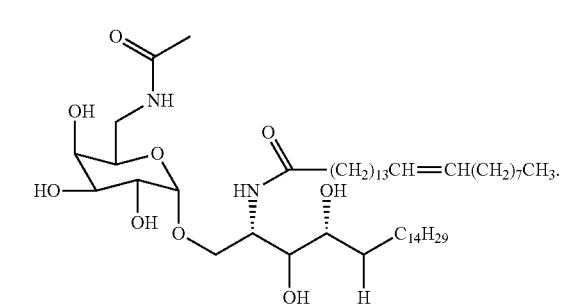

25. The method of claim 13, wherein the compound is
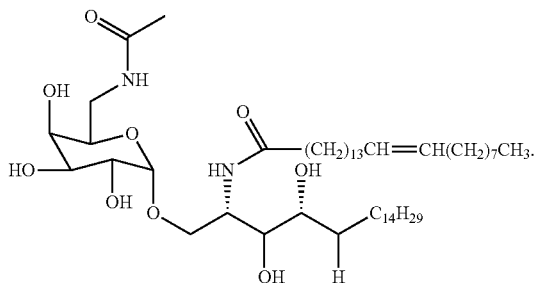
26. The method of claim 21, wherein the compound is
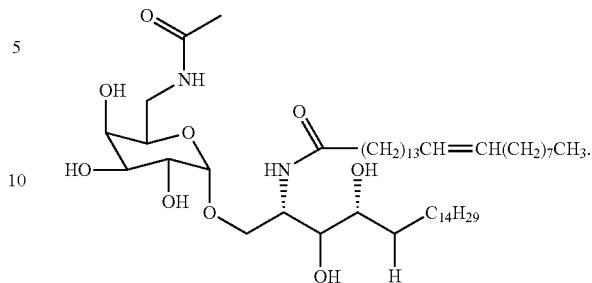
27. The method of claim 1, wherein $R_1$ is $C(O)R_{13}$.
28. The method of claim 27, wherein $R_{13}$ is $C_1$-$C_{12}$ alkyl.
* * * * *

UNITED STATES PATENT AND TRADEMARK OFFICE
CERTIFICATE OF CORRECTION

| | | |
|---|---|---|
| PATENT NO. | : 8,227,581 B2 | Page 1 of 1 |
| APPLICATION NO. | : 12/296169 | |
| DATED | : July 24, 2012 | |
| INVENTOR(S) | : Savage et al. | |

It is certified that error appears in the above-identified patent and that said Letters Patent is hereby corrected as shown below:

Col. 5, line 5: "is . In further" should read -- is $C_{13}H_{27}$. In further --

Col. 5, line 7: "$R_8$ is not $C_{13}H^{27}$. Structures" should read -- $R_8$ is not $C_{13}H_{27}$. Structures --

Signed and Sealed this
First Day of January, 2013

David J. Kappos
*Director of the United States Patent and Trademark Office*